(12) United States Patent
Schaer et al.

(10) Patent No.: US 6,522,930 B1
(45) Date of Patent: *Feb. 18, 2003

(54) IRRIGATED ABLATION DEVICE ASSEMBLY

(75) Inventors: Alan K. Schaer, San Jose, CA (US); Aurelio Valencia, East Palo Alto, CA (US)

(73) Assignee: Atrionix, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/073,907

(22) Filed: May 6, 1998

(51) Int. Cl.⁷ .................................................. A61F 2/00

(52) U.S. Cl. ........................ 607/101; 607/104; 607/105; 606/41

(58) Field of Search ........................ 606/41, 42, 27–29, 606/31–32; 607/96, 98, 100, 101, 102, 104, 105, 113, 115, 116, 119, 122; 600/372, 374, 381

(56) References Cited

U.S. PATENT DOCUMENTS

| | | | |
|---|---|---|---|
| 4,650,457 A | * | 3/1987 | Morioka et al. ............... 604/4 |
| 4,850,351 A | | 7/1989 | Herman et al. |
| 5,348,554 A | | 9/1994 | Imran et al. |
| 5,368,564 A | * | 11/1994 | Savage ........................ 604/95 |
| 5,370,678 A | | 12/1994 | Edwards et al. |
| 5,423,811 A | | 6/1995 | Imran et al. |
| 5,433,708 A | | 7/1995 | Nichols et al. |
| 5,435,805 A | * | 7/1995 | Edwards et al. ............... 604/22 |
| 5,505,730 A | | 4/1996 | Edwards |
| 5,545,161 A | | 8/1996 | Imran |
| 5,558,672 A | | 9/1996 | Edwards et al. |
| 5,562,720 A | | 10/1996 | Stern et al. |
| 5,569,241 A | | 10/1996 | Edwards |
| 5,575,788 A | | 11/1996 | Baker et al. |
| 5,582,609 A | | 12/1996 | Swanson et al. |
| 5,588,432 A | | 12/1996 | Crowley |
| 5,643,197 A | | 7/1997 | Brucker et al. |
| 5,658,278 A | | 8/1997 | Imran et al. |
| 5,676,693 A | | 10/1997 | LaFontaine |

(List continued on next page.)

FOREIGN PATENT DOCUMENTS

| | | |
|---|---|---|
| EP | 0 472 368 A2 | 2/1992 |
| EP | 0 711 573 A1 | 5/1996 |
| EP | 0 856 292 A1 | 8/1998 |
| FR | 1466248 | 1/1967 |
| WO | WO 90/07909 | 7/1990 |
| WO | WO 95/10318 | 4/1995 |
| WO | WO 95/34346 | 12/1995 |
| WO | WO 97/32525 | 9/1997 |
| WO | WO 97/37607 | 10/1997 |
| WO | WO 97/45156 | 12/1997 |
| WO | PCT/US98/14220 | 8/1998 |
| WO | WO 99/00064 | 1/1999 |

*Primary Examiner*—Rosiland S. Kearney
(74) *Attorney, Agent, or Firm*—Knobbe, Martens, Olson & Bear, LLP

(57) ABSTRACT

A tissue ablation device assembly ablates a region of tissue of a body space wall of a patient. In a tissue ablation device assembly, an ablation member is disposed on the distal end portion of an elongated body. The ablation member includes an ablation element and at least one conductor coupled to the ablation element. A porous membrane covers the ablation element and defines an inner space between the ablation element and an inner surface of the porous membrane. A pressurizable fluid passageway extends between a fluid port on the proximal end portion of the elongated body and the inner space within the porous membrane. Fluid can pass from the fluid port, through the pressurizable fluid passageway, to the inner space. The porous membrane allows a volume of pressurized fluid to pass through the porous membrane to an exterior of the ablation member so as to irrigate the ablation element.

28 Claims, 11 Drawing Sheets

U.S. PATENT DOCUMENTS

| | | |
|---|---|---|
| 5,681,308 A | 10/1997 | Edwards et al. |
| 5,687,723 A | 11/1997 | Avitall |
| 5,697,927 A | 12/1997 | Imran et al. |
| 5,720,775 A | 2/1998 | Larnard |
| 5,769,846 A | 6/1998 | Edwards et al. |
| 5,797,903 A | 8/1998 | Swanson et al. |
| 5,797,905 A | 8/1998 | Fleischman et al. |
| 5,800,432 A | 9/1998 | Swanson |
| 5,800,484 A * | 9/1998 | Gough et al. ............... 607/104 |
| 5,807,395 A | 9/1998 | Mulier et al. |
| 5,840,031 A | 11/1998 | Crowley |
| 5,840,076 A | 11/1998 | Swanson et al. |
| 5,843,154 A | 12/1998 | Osypka |
| 5,895,355 A * | 4/1999 | Schaer ....................... 600/381 |
| 5,919,188 A * | 7/1999 | Shearon et al. ............... 606/41 |
| 6,010,500 A * | 1/2000 | Sherman et al. .............. 606/41 |
| 6,032,077 A * | 2/2000 | Pomeranz ................... 607/101 |
| 6,064,902 A | 5/2000 | Haissaguerre et al. |
| 6,071,279 A | 6/2000 | Whayne et al. |
| 6,071,281 A | 6/2000 | Burnside et al. |
| 6,080,151 A * | 6/2000 | Swartz et al. ................. 606/45 |

* cited by examiner

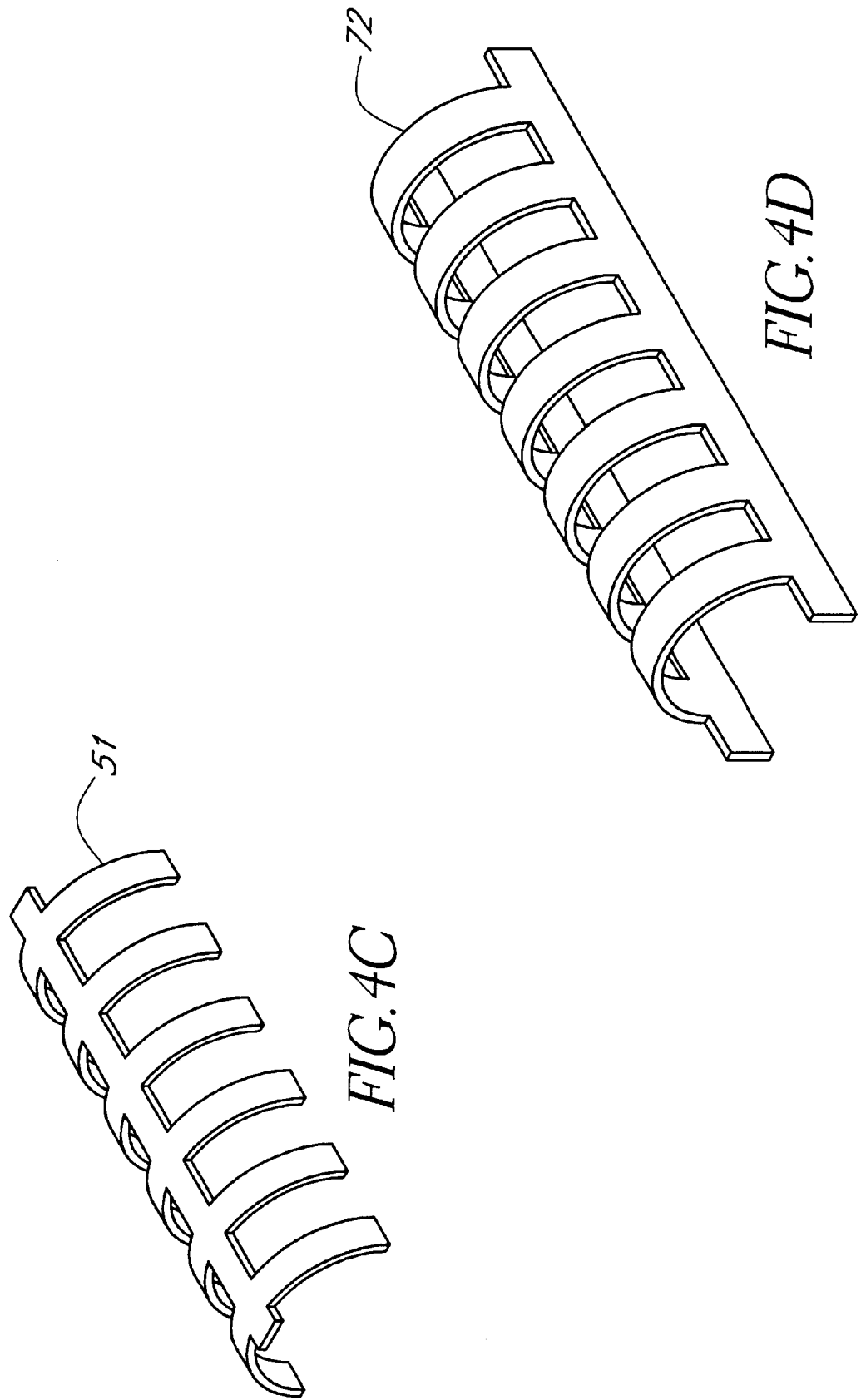

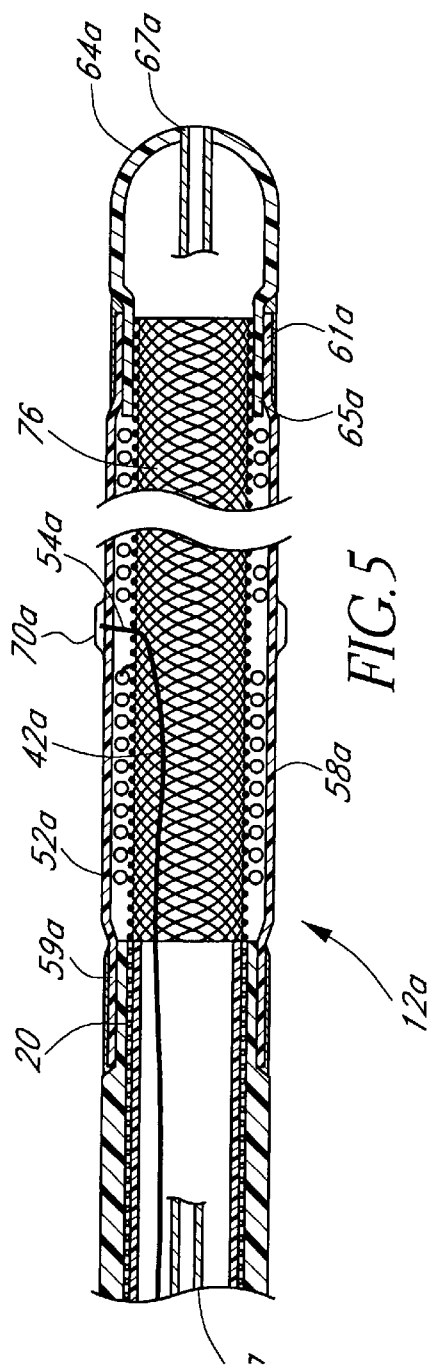
FIG.5
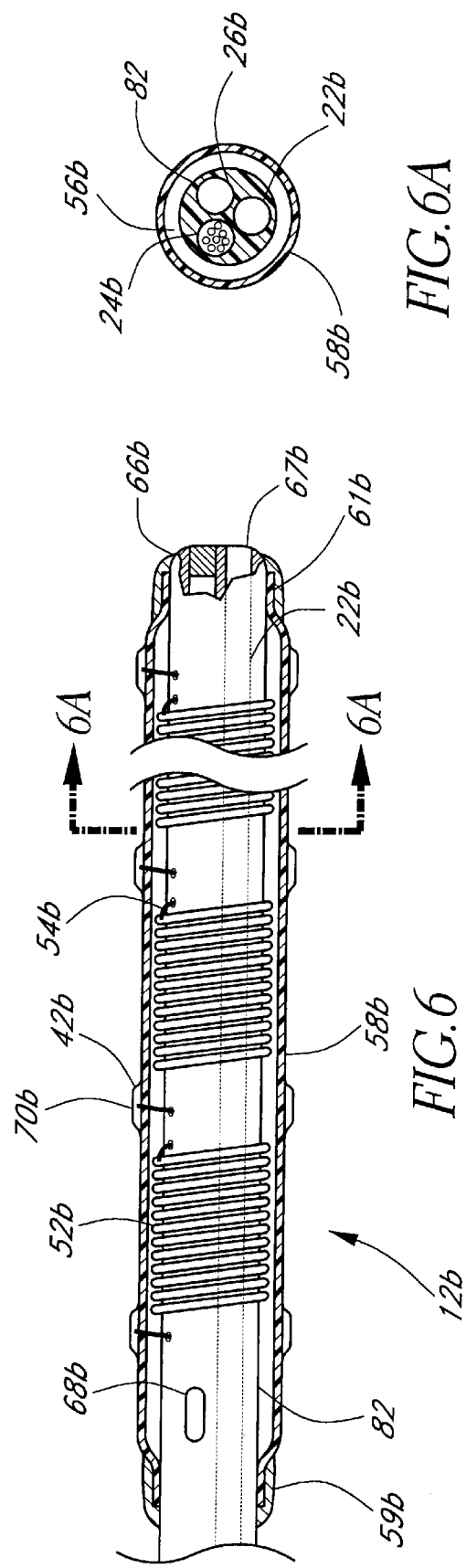
FIG.6A
FIG.6

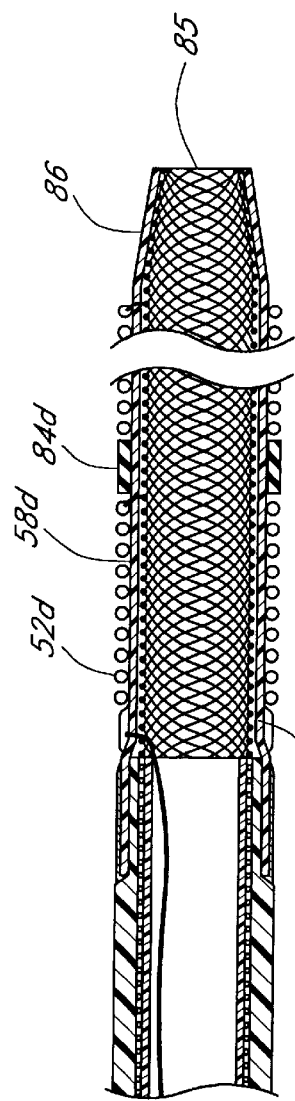
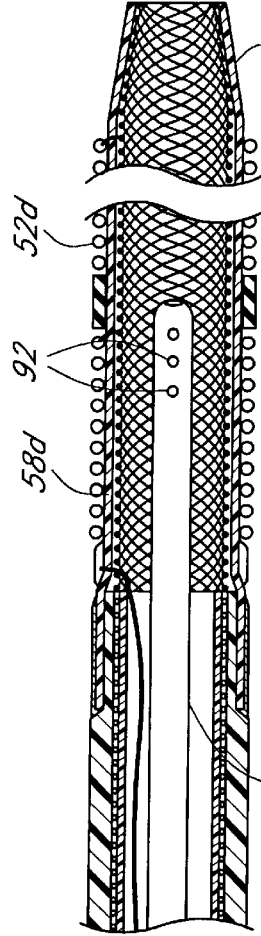
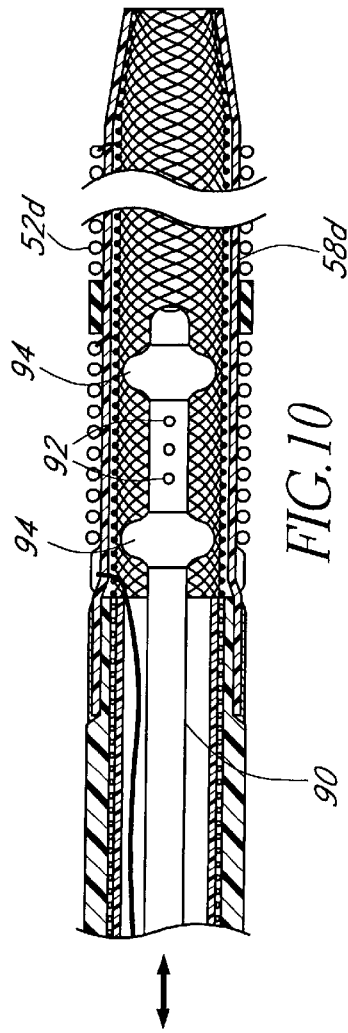

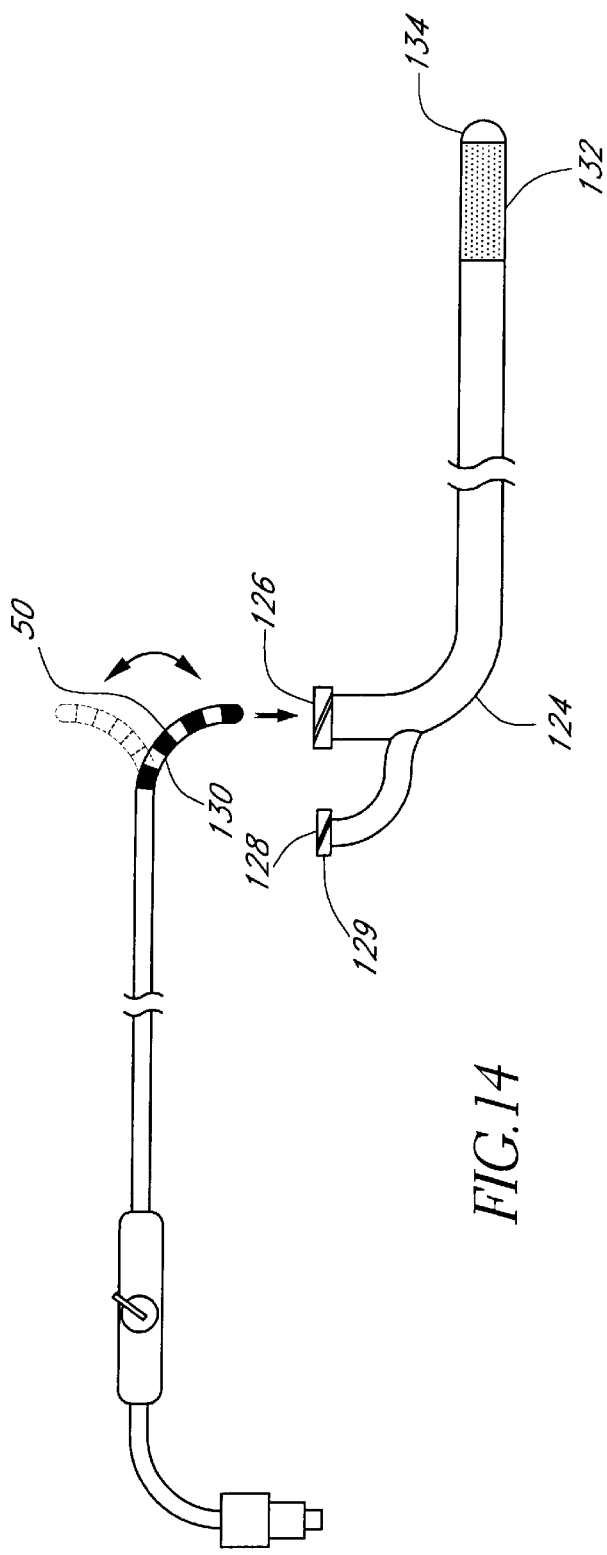
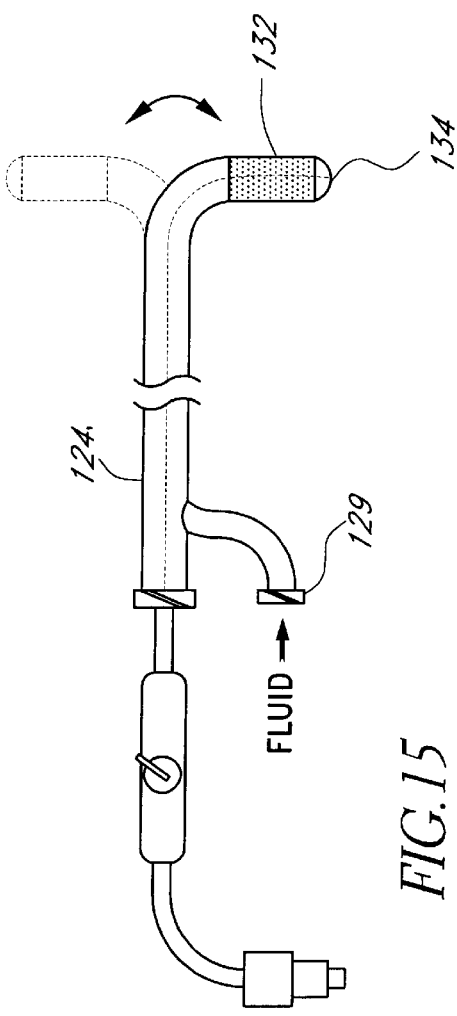
FIG.14
FIG.15

IRRIGATED ABLATION DEVICE ASSEMBLY

BACKGROUND OF THE INVENTION

1. Field of the Invention

The present invention is a surgical device. More specifically, the present invention relates to a tissue ablation device assembly with an irrigated ablation member which is adapted to produce a lesion within tissue. The present invention also relates to the construction of the ablation member.

2. Description of Related Art

Cardiac arrhythmias, and atrial fibrillation in particular, remain a persistent medical condition in modern society. Persistence of atrial fibrillation has been observed to cause or at least contribute to various medical conditions including congestive heart failure, stroke, other thromboembolic events, and myocardial ischemia.

Several surgical approaches have been developed for the purpose of treating or preventing cardiac arrhythmias, and in particular more recently with the intention of treating atrial fibrillation, such as according to one example known as the "maze procedure," as disclosed by Cox, J L et al. in "The surgical treatment of atrial fibrillation. I. Summary" *Thoracic and Cardiovascular Surgery* 101(3), pp. 402–405 (1991); and also by Cox, J L in "The surgical treatment of atrial fibrillation. IV. Surgical Technique", *Thoracic and Cardiovascular Surgery* 101(4), pp. 584–592 (1991). In general, the "maze" procedure is designed to relieve atrial arrhythmia by restoring effective atrial systole and sinus node control through a prescribed pattern of incisions about the cardiac tissue wall. In the early reported clinical experiences, the "maze" procedure included surgical incisions in both the right and the left atrial chambers. However, more recent reports predict that the surgical "maze" procedure may be substantially efficacious when performed only in the left atrium, such as is disclosed in Sueda et al., "Simple Left Atrial Procedure for Chronic Atrial Fibrillation Associated With Mitral Valve Disease" (1996).

The "maze procedure" as performed in the left atrium generally includes forming vertical incisions from the two superior pulmonary veins and terminating in the region of the mitral valve annulus, traversing the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the precipitating conduction to the atrial arrhythmia by creating conduction blocks within the aberrant electrical conduction pathways.

While surgical intervention such as the "maze" procedure has been moderately successful in treating atrial arrhythmia, this highly invasive methodology is believed to be prohibitive in many cases. However, these procedures have provided the principle that electrically isolating faulty cardiac tissue may successfully prevent atrial arrhythmia, and particularly atrial fibrillation caused by perpetually wandering reentrant wavelets or focal regions of arrhythmogenic conduction. Hence the development of less invasive catheter-based approaches to treat atrial fibrillation through cardiac tissue ablation intended to emulate the maze-type procedures.

In general, known catheter-based therapies for cardiac arrhythmias involve introducing a catheter within a cardiac chamber, such as in a percutaneous translumenal procedure, such that an energy sink on the catheter's distal end portion is positioned at or adjacent to the aberrantly conductive tissue. The energy sink is activated according to various known modes of operation such that the targeted tissue adjacent thereto is ablated and rendered non-conductive as to the propagation of cardiac rhythm.

One particular type of energy sink which has been disclosed for use as an ablation element as such is a heat sink which ablates tissue by use of thermal conduction, for example by means of a resistive wire which heats upon application of a current in a closed loop system within an ablation catheter. A threshold temperature which has been disclosed for ablating tissue according to a thermal conduction mode of ablation is generally above 45 degrees, usually from 45 to 70 degrees, usually 50 to 65 degrees C., and preferably from about 53 to 60 degrees C. It has also been observed that high temperatures, such as temperatures above 70 degrees, may produce charring at the tissue-ablation element interface. It has been further observed that such charring may cause adverse medical results such as thrombosis on the tissue wall in the case of tissue ablation of the cardiac chambers including the atrium.

Another previously disclosed energy sink for use as an ablation element includes an electrode which emits direct current (DC), such as from an electrode on the distal end of a catheter placed adjacent to the targeted tissue and coupled by way of the body's own conductivity to a return electrode. However, more modem current-based ablation elements which have been disclosed for use in tissue ablation devices and procedures instead use radio frequency (RF) current driven electrodes. According to RF electrode ablation, the electrode is placed adjacent to the target tissue and is electrically coupled to a return electrode which may be provided on the same or another invasive device, or more generally is provided as a large surface area conductive patch provided on the patient. Current flowing between the electrode and the patch is at its highest density at the tissue adjacent to the treatment electrode and therefore causes ablation of the tissue. It is believed that this arrangement is adapted to ablate tissue both by way of thermal conduction at the electrode-tissue interface, in addition to thermal ablation caused by resistive or dielectric heating of the tissue itself as it resides in the high current density region of the RF current path.

In addition to the energy sinks just described for use as tissue ablation elements, other energy sources which have been disclosed for use in catheter-based ablation procedures include microwave energy sources, cryoblation energy sources, light energy sources, and ultrasound energy sources.

Various specific catheter-based tissue ablation devices and methods have also been disclosed for forming lesions of specific geometry or patterns in the target tissue. In particular, various known tissue ablation devices have been adapted to form either focal or linear (including curvilinear) lesions in the wall tissue which defines the atrial chambers. Less-invasive percutaneous catheter ablation devices and techniques have been disclosed which use variations of "end-electrode" catheter designs for delivering a point source of energy to ablate the area of abnormal electrical activity, such as where atrial fibrillation is believed to be focal in nature, such as where a focal arrhythmia originates from a pulmonary veins of the left atrium. The end electrodes form localized lesions that ablate the focus, thus ablating and thereby treating such focal arrhythmias, such as in the pulmonary veins. Examples of previously disclosed therapeutic focal ablation procedures for ablating foci in the pulmonary vein may be found in the following references: "Right and Left Atrial Radiofrequency Catheter Therapy of Paroxysmal Atrial Fibrillation", Haissaguerre et al., *Journal of Cardiovascular Electrophysiology* 7(12), pp. 1132–1144 (1996); and "A focal source of atrial fibrillation treated by discrete radiofrequency ablation", Jais et al., *Circulation* 95:572–576 (1997).

Focal tissue ablation, however, is not generally believed to be appropriate for many cases of atrial fibrillation of the "multi-wavelet" type which involve multiple reentrant loops which are believed to arise from various arrhythmogenic sources. These multiple excitation waves would simply circumnavigate a focal ablative lesion within the cardiac tissue. Therefore, similar to the surgical "maze" procedure described above, continuous linear lesions are believed to be necessary in order to completely segment the atrial tissue so as to block the wave fronts associated with most forms of atrial fibrillation. Therefore, other specific tissue ablation devices have also been disclosed which are adapted to make linear lesions for the particular purpose of treating and preventing this multi-wavelet form of atrial fibrillation.

Various tissue ablation device assemblies and methods of use have been disclosed for making linear lesions with a single distal electrode tip adapted to either drag or form sequential point lesions along a tissue wall, herein referred to as "drag" assemblies and procedures. According to one disclosed form of a true drag procedure, as the RF energy is being applied, the catheter tip is drawn across the tissue along a predetermined pathway within the heart. Alternatively, lines of ablation using distal tip electrode catheter assemblies can be made by sequential positioning and ablation along the pathway.

In one particular example intended to use single point electrode catheter assemblies to form linear lesions in a maze-type procedure, shaped guiding sheaths are used to position an end electrode on a deflectable or shaped catheter along a predetermined path of tissue to be ablated. According to this disclosed assembly and method, a continual, transmural lesion must be made by remote, percutaneous manipulation of the device using only the means of X-ray fluoroscopy for visualizing catheter location in the beating cardiac chamber. Moreover, it has been observed that this process may fail to produce continuous, transmural lesions, thus leaving the opportunity for the reentrant circuits to reappear in the gaps remaining between point or drag ablations, and in many cases requiring.

Further more detailed examples of tissue ablation device assemblies which use sequential application of energy from a point on a catheter which is remotely manipulated to ostensibly create an ablation maze according to a predetermined pattern, such as according to the examples just described, are disclosed in the following references: U.S. Pat. No. 5,427,119 to Swartz et al.; U.S. Pat. No. 5,564,440 to Swartz et al.; U.S. Pat. No. 5,575,766 to Swartz et al.; and U.S. Pat. No. 5,690,611 to Swartz et al.

In addition to the "drag" type procedures described above using end electrode catheters to form linear lesions, other assemblies have been disclosed which provide multiple electrodes along a length of the distal end portion of a catheter in order to form lines of conduction block along cardiac chamber wall tissue adjacent to the multi-electrode segment. These catheter assemblies generally include a plurality of ring or coil electrodes circling the catheter at spaced intervals extending proximally from the distal tip of the catheter.

According to several disclosed examples of "multi-electrode" tissue ablation devices of this type (and also further according to various designs of the "end-electrode"-type), a catheter upon which a linear electrode array is positioned is provided with a steerable tip. These catheters generally include one or more steering wires, extending from a steering mechanism at the proximal end of the catheter to an anchor point at the distal end of the catheter. By applying tension to the steering wire or wires, the tip of the catheter can be deflected at least along one plane which at least in-part allows the catheter's distal end with electrodes to be steered to a desired direction. Furthermore, at least one other known tissue ablation catheter comprise a rotatable steering feature which allows the distal end of the catheter to be rotated about its longitudinal axis by manipulating the proximal end of the catheter. Once the catheter is steered and positioned against a predetermined region of body tissue within a body chamber according to these various disclosed assemblies, ablating elements may be activated to form a lesion.

Tissue ablation device assemblies have also been designed wherein a catheter having a predetermined curve is received within a sheath that is advanced over the distal end of the catheter. Advancement of the catheter within the sheath modifies the predetermined curve of the distal end of the catheter. By inserting different shaped guide catheters through the outer guide catheter, different shapes for the distal end of the catheter are created. Other disclosed linear lesion assemblies include preshaped catheters with electrodes along the shaped portion, including "hairpins" or "J-shapes".

More detailed examples of catheter-based tissue ablation devices and methods for forming long linear lesions in tissue along the walls of the atrial chambers, such as according to at least some of the examples just described, are disclosed in the following disclosure: U.S. Pat. No. 5,545,193 to Fleischman et al.; U.S. Pat. No. 5,549,661 to Kordis et al.; U.S. Pat. No. 5,617,854 to Munsif; PCT Publication WO 94/21165 to Kordis et al.; and PCT Publication WO 96/26675 to Klein et al. The disclosures of these references are herein incorporated in their entirety by reference thereto.

During tissue ablation procedures, and particularly of the RF ablation type, it is critical to maintain precise positioning and contact pressure of the ablation electrode or electrodes against the cardiac tissue to create a continuous, linear lesion to properly treat the arrhythmic condition. Therefore, more recently disclosed catheter-based cardiac tissue ablation assemblies and methods are adapted to include more complex mechanisms for manipulating and positioning the ablation element precisely and securely at desired locations in a cardiac chamber and also for forming particularly desired lesion patterns in such chambers. Previously disclosed catheters of this type include: a three dimensional basket structure with single or multiple electrodes which are moveable along a plurality of spines which are intended to be held in place along tissue by means of the expanded basket in the atrium; a device having flexible electrode segments with an adjustable coil length which may form a convoluted lesion pattern with varying length; a composite structure which may be variously flexed along its length to form a variety of curvilinear shapes from a generally linear shape; proximally constrained diverging splines which expand upon emergence from an opening in the distal end of an elongated catheter and having a multi-electrode element extending therebetween; a probe device having an ablation element which is adapted to bend or bow outwardly of the probe and against a desired region of tissue; and a device having an outer delivery sheath and an elongated electrode device slideably disposed within the inner lumen of the delivery sheath such that proximal manipulation of the electrode device causes its distal multi-electrode section to arch, or "bow" outwardly away from the distal section of the delivery sheath.

More detailed examples of catheter-based tissue ablation assemblies and methods for creating long linear lesions in cardiac tissue, such as according to the types just described, are variously disclosed in the following references: U.S. Pat. No. 5,592,609 to Swanson et al.; U.S. Pat. No. 5,575,810 to Swanson et al.; PCT Published Application WO 96/10961 to Fleischman et al.; U.S. Pat. No. 5,487,385 to Avitall; U.S. Pat. No. 5,702,438 to Avitall; U.S. Pat. No 5,687,723 to Avitall; and PCT Published Application WO 97/37607 to Schaer. The disclosures of these references are herein incorporated in their entirety by reference thereto.

In addition to those known assemblies just summarized above, additional tissue ablation device assemblies have also been recently developed for the specific purpose of ensuring firm contact and consistent positioning of a linear ablation element along a length of tissue by anchoring the element at least at one predetermined location along that length, such as in order to form a "maze"-type lesion pattern in the left atrium. One example of such assemblies includes an anchor at each of two ends of a linear ablation element in order to secure those ends to each of two predetermined locations along a left atrial wall, such as at two adjacent pulmonary veins, so that tissue may be ablated along the length of tissue extending therebetween.

Fluid Irrigated Ablation Elements

In addition to the various catheter and ablation element features just described above according to various known tissue ablation device assemblies, other assemblies have also disclosed which provide a means for coupling an ablation element to a controlled flow of fluid for the purpose of enhancing the ablative response of tissue at the tissue-ablation element interface, which resulting ablation elements are referred to "fluid irrigated" ablation elements or electrodes.

For example, one previously disclosed tissue ablation device which is intended for thermal ablation of hollow body organs (disclosed examples include gallbladder, the appendix, the uterus, the kidney) or hollow body passages (disclosed examples include blood vessels, and fistulas) by heating such tissues provides a managed flow of thermally conductive fluid medium flows across a resistive heating wire disposed over a catheter body. The thermally conductive fluid medium is intended to enhance and provide uniformity of heat transfer from the resistance heater coil, and is provided to the heater coil at a temperature from 37 to 45 degrees C. in order to shorten the time necessary to raise the temperature of the medium to the treatment temperature. In one particular disclosed variation this assembly and method, the fluid flows from a tube and through apertures between turns of the wire disposed over the tube. In another disclosed variation of this example, the fluid flows through a heating element which may be a perforate or permeable structure such as a wire mesh or other perforate cylindrical structure. In still a further disclosed variation, the fluid medium flow oscillates, where volume of the fluid is alternatively infused and aspirated from the region of the heater coil in order to control temperature in that region.

More detailed examples of tissue ablation device assemblies and methods which couple thermally conductive fluid medium to a resistive heating element for the purpose of enhancing heat transfer to tissue is disclosed in U.S. Pat. No. 5,433,708 to Nichols et al.

Other previously disclosed tissue ablation devices, in particular ablation devices of the RF electrode variety, are also adapted to couple fluid to the tissue-ablation element interface, such as for the intended purpose of cooling the tissue during RF ablation, due at least in-part to the narrow ranges of acceptable tissue temperatures for such ablation as described previously above. According to this intended fluid cooling function, various other means have also been disclosed for controlling the temperature at the tissue-ablation element interface during ablation, for example including assemblies using feedback control of the amount of energy or current flowing to and from the ablation element based upon measured temperature or impedance at the tissue interface. In addition, another intended result for previously disclosed fluid irrigated RF electrode assemblies, particularly those of the multi-electrode type for forming linear maze-type lesions such as described above, is to evenly distribute the current density flowing into the tissue along the length of the RF ablation element.

For example, several previously disclosed fluid-coupled RF ablation assemblies and methods use fluid to cool an electrode element during RF ablation by circulating the fluid internally through the catheter, including through a chamber formed by an inner surface or backing of the electrode. Such assemblies intend to cool the tissue-electrode interface by cooling the electrode itself during ablation, and include those of the "end-electrode"-type, further including such assemblies of the deflectable tip/steerable variety, in addition to assemblies adapted with larger surface ablation elements for forming large lesions, such as for making linear lesions in maze-type procedures. In one further disclosed example, a passive heat conduction means is coupled to the interior of an end electrode and is made up of a fibrous material such as cotton fibers which have been impregnated with a heat absorbing fluid such as saline or water. As the end electrode heats during ablation, the temperature is conducted away from the electrode, into the passive heat conduction means where it is dissipated toward a cooler portion.

Other disclosed variations of fluid cooled RF ablation assemblies include ports through which the cooling fluid may flow outwardly from the catheter to enhance the cooling thermal transfer from the electrode to the fluid. In one known example of this type, the fluid flows through apertures in the ablation catheter adjacent to the electrode, and in alternatively disclosed variations fluid flows through apertures in the electrode itself. In another previously disclosed tissue ablation assembly of the end-electrode type, a plurality of lumens include distal ports adjacent to the end electrode and are adapted to allow cooling fluid to flow over the exterior surface of the electrode adjacent to the tissue-electrode interface at the electrode's tip.

Other examples of known tissue ablation device assemblies using fluid irrigated electrodes are instead adapted to provide fluid irrigation directly to the tissue-electrode interface. In one known example of this type, apertures are formed in a metallic end-electrode at its distal arcuate surface or tip where the electrode is intended to contact the target tissue. This assembly is intended to provide a path for internally circulating fluid within the chamber formed by the end electrode to flow into the tissue-electrode interface during ablation.

Another example of a tissue ablation device intended to ablate an inner layer of an organ in the body, and more particularly the endometrium, includes an inflatable member with an interior that houses an electrolytic solution such as saline. The balloon has a back side, and a front side that includes a plurality of apertures. The electrolytic solution is permitted to selectively flow from the interior through the apertures at a flow rate that is dependent on the pressure applied to the balloon by the electrolytic solution. A conforming member includes a conductive surface and a back side oriented toward the perforate front side of the balloon. The conforming member is further disclosed to be between 0.01 and 2.0 centimeters thick, and may be made of an open cell foam or thermoplastic film material which is adapted to conform to the irregular inner surface the endometrium, such as silicon reinforced natural gum rubber, neoprene, soft gum rubber, and polyurethane material. The disclosed construction for the conductive surface of the conforming member includes extruded conductive materials forming the member itself, implanted conductive ions onto the member, or a conductive surface coating such as in the form of a printed circuit. According to one further disclosed optional embodiment of this assembly, a relatively strong membrane may be positioned between the balloon and the conforming member and passes the electrolytic fluid from the balloon to the conforming member. The optional membrane is further disclosed to be made of a microporous material such as mylar, expanded PFT such as Gortex available from Gore Company.

According to the disclosed method of use for this assembly, the back side of the balloon presses against the interior of the uterus. As pressure within the balloon increases with electrolytic fluid, the conforming member confronts the opposite wall of the endometrium. The combination of the conforming member and the application of electrolytic solution through the conforming member is further disclosed to provide for the effective delivery of RF energy to the endometrium.

In a further disclosed variation of the endometrial ablation device assembly just described, a balloon having a plurality of apertures through its outer skin has a particular shape when expanded which approximates that of the inter-uterine space. A conforming member similar to the type just described for the previous assembly is provided substantially around the outer surface of the balloon and is further adapted to be compressible to thereby conform to the endometrium. A printed circuit is provided as an ablation element and can be formed in or on the conforming member, or adjacent to its backside or conductive surface and delivers RF energy to selected sections of the endometrium. Fluid flows through the apertures in the balloon, through the foam-like conforming member, and into the endometrium during ablation. An optional porous membrane is further disclosed which is positioned between the conforming member and the balloon.

Various additional variations of the endometrial ablation assemblies just described have also been disclosed. In one such disclosure, the expandable member which forms the balloon may be made of a microporous material that does not include distinct apertures. Further disclosed compositions for the foam-like conforming member to adapt it to be moldable and formable to irregular surfaces of the endometrium include knitted polyester, continuous filament polyester, polyester-cellulose, rayon, polyimide, polyurethane, polyethylene. In still a further disclosed embodiment, zones of lower porosity may be created along the outer surface of the device by sealing two conforming members together about an electrode in order to retain electrolytic solution at the electrode to elevate the temperature there and create a larger ablative electrode effect. In one more detailed disclosure of this configuration, two pieces of UltraSorb foam were sealed between 0.004 inch by 0.016 inch flat electrode wire with about 1.0 inch of SST wire exposed in the foam. Various further disclosed foam sizes of this variety include thicknesses of: (i) $\frac{1}{16}$ inch by $\frac{1}{8}$ inch, (ii) $\frac{1}{8}$ inch by $\frac{1}{16}$ inch; and (iii) $\frac{1}{16}$ inch by $\frac{1}{16}$ inch, wherein the foam size was about 1.0 inch by 1.0 inch.

Another example of a known fluid irrigated tissue ablation electrode device assembly intended for use in creating a linear lesion in a maze-type procedure in the atrium includes a fluid irrigated linear lesion electrode element on a catheter having a removable preshaped stylet intended to conform the region of the ablation element to the inner surface of the atrium. A foam layer formed of open cell polyurethane, cotton-like material, open-cell sponge, or hydrogels is disposed over the electrode element and is permeable by conductive fluids and exhibits some compressibility. The foam layer is enclosed within a fluid impermeable covering which includes a plurality of tiny holes intended to help focus the RF energy onto the target tissue within the heart. The covering is formed of heat shrink polyethylene, silicone, or other polymeric material comprised of conduction wires or flat conductive ribbons which are insulated but stripped of the insulation at spaced intervals along the ablation section. Conductive fluid flows over the electrode element through a lumen in the catheter shaft, through holes in the catheter shaft, to the compressible foam layer, and through the perforated covering during ablation. The electrode element according to this variation is formed of a conductive wire or flat ribbon extending along the lumen with selected insulated and non-insulated portions.

Still a further known tissue ablation device assembly which is intended to form linear maze-type lesions in an atrium includes the use of fluid irrigated electrodes along a loop which is adapted to be positioned within the heart such that the ablation section on one side of the loop is leveraged against a chamber wall by action of the opposite side of the loop against an opposing chamber wall. A plurality of electrodes are positioned over an infusion tube with holes. A compressible foam layer is positioned over the electrodes and is covered by a covering which is perforated with discrete holes. Fluid flows from the infusion tube, through the holes in the tube and past the energized electrodes, through the foam layer, and finally outward through the holes in the outer covering during ablation. A conductive fluid such as conductive saline may be used in a manner to create a conductive path between the electrodes and the target tissue, and also to cool the ablation electrodes.

Other more detailed examples of ablation devices which flow fluid between electrodes and tissue when current is flowing from the electrodes to the tissue, such as according to the examples just described, are disclosed in the following references: U.S. Pat. No. 5,348,554 to Imran et al.; U.S. Pat. No. 5,423,811 to Imran et al.; U.S. Pat. No. 5,505,730 to Edwards; U.S. Pat. No. 5,545,161 to Imran et al.; U.S. Pat. No. 5,558,672 to Edwards et al.; U.S. Pat. No. 5,569,241 to Edwards; U.S. Pat. No. 5,575,788 to Baker et al.; U.S. Pat. No. 5,658,278 to Imran et al.; U.S. Pat. No. 5,688,267 to Panescu et al.; U.S. Pat. No. 5,697,927 to Imran et al.; PCT Patent Application Publication No. WO 97/32525 to Pomeranz et al.; and PCT Patent Application Publication No. WO 98/02201 to Pomeranz et al.

None of the cited references discloses a tissue ablation member having an ablation element with a length that is covered and enclosed by a single, thin layer of a porous fluid-permeable membrane which is adapted to communicate with a pressurizable fluid source in order to irrigate the tissue-ablation element interface with fluid from that fluid source in an even manner along the ablation element length.

Nor do the cited references disclose a tubular member with a distal fluid permeable portion that is adapted to slideably receive a tissue ablation device such that an ablation element along the ablation device is positioned within the fluid permeable portion so a conductive fluid may be infused over the ablation device within the tube, over the ablation element, and outwardly through the permeable portion and into a tissue-ablation element interface along the fluid permeable portion.

SUMMARY OF THE INVENTION

The present invention relates to a medical device assembly for ablating a region of tissue of a body space wall which defines at least in part a body space in a patient.

One aspect of the present invention involves a tissue ablation device assembly which includes an ablation member having at least one ablation element, at least one conductor which is coupled to and extends proximally from the ablation element, and at least one porous membrane. The porous membrane, which includes a generally non-compressible porous wall having an inner surface that defines an inner space, is adapted to allow a volume of pressurized fluid to pass from the space within the porous membrane through the porous wall to an exterior of the ablation member. The ablation element is positioned in sufficiently close proximity to the porous membrane so that the fluid emanating from the porous membrane flows at least partially between tissue of a patient and the ablation element. In addition, at least one fluid pressurizable passageway of the ablation member communicates with the inner space.

In one variation of this assembly, the porous membrane covers the ablation element which is disposed within the inner space. In another variation of this assembly, at least a portion of the ablation element lies on an outer side of the porous membrane. In either case, the assembly allows for fluid irrigation of the electrodes with multiple layers.

In an additional variation of this assembly, the ablation member is disposed on a distal end of an elongated body. First and second anchors are arranged on the elongated body and the ablation member is located between the anchors. Further to this variation, at least one of the anchors is a guidewire tracking member which forms a bore that is adapted to advance a corresponding portion over the elongated body of a guidewire.

Another aspect of the present invention is a tissue ablation device assembly which includes an ablation member having an ablation element, at least one conductor coupled to and extending proximally from the ablation element, and at least one porous membrane. The porous membrane has a generally non-compressible porous wall with an inner surface that defines an inner space and covers the ablation element disposed within the inner space. The ablation member also includes at least one pressurizable fluid passageway which communicates with the inner space. The porous membrane is adapted to allow a volume of pressurized fluid to pass from the inner space through the porous wall to an exterior of the ablation member.

In a variation of this assembly, the tissue ablation device assembly additionally includes an elongated body having a proximal end portion and distal end portion. The ablation member is included on the distal end portion of the elongated body. The pressurizable fluid passageway extends between a proximal fluid port along the proximal end portion of the elongated body and the inner space within the porous membrane. The conductor, which extends proximally from the ablation element, terminates proximally along the proximal end portion of the elongated body.

An additional aspect of this invention involves a tissue ablation device assembly including a sheath member having a proximally end portion and a distal end portion. The sheath member includes a porous membrane, a fluid delivery passageway and a proximal fluid coupler. The porous membrane has a porous wall which is adapted to be positioned within a body space in a patient by manipulating the proximal end portion of the sheath member which is external of the patient. The porous membrane defines an inner space, which is sized to slideably receive a distal end of a catheter. The inner space is defined at least in part by an inner surface of the porous wall. The porous membrane is adapted to allow a volume of fluid within the inner space to be pressurized to a predetermined pressure and to pass from within the inner space, through the porous wall and to an exterior of the sheath member. The fluid delivery passageway extends from the inner space to a proximal port, which is located on the proximal end portion of the sheath member. Located on the proximal end portion, the fluid coupler is adapted to fluidly couple the proximal port with a pressurized fluid source.

In one variation of this assembly, the tissue ablation device assembly also includes an ablation catheter having outer surface, a proximal end section and a distal end section with an ablation element. A conductor is coupled to and extends proximally from the ablation element and terminates proximally along the proximal end section of the ablation catheter. A proximal ablation coupler couples the conductor and ablation element to an ablation actuator. A pressurized fluid source is coupled to the proximal fluid coupler. The distal end section of the ablation catheter is adapted to slideably engage the porous member such that the ablation element may be positioned within the porous wall such that a volume of fluid from the pressurized fluid source passes between an outer surface of the ablation catheter and an inner surface of the fluid delivery passageway.

Another aspect of this invention is a method of constructing an elongated medical article. The method involves providing first and second tubular members. At least one opening is formed within a section of the first tubular member. The section of the first tubular member is positioned at least partially over the second tubular member. A seal member comprised of a material compatible with the material of the second tubular member is provided and positioned over at least a portion of the section of the first tubular member. The seal member is fused with the second tubular member to form a fused assembly with a portion of the fused assembly extending through the opening formed in the section of the first tubular member to fix together the first and second tubular members.

Further aspects, features and advantages of the present invention will now become apparent from a detailed description of the preferred embodiment which follows.

BRIEF DESCRIPTION OF THE DRAWINGS

The above-mentioned and other features of the invention will now be described with reference to the drawings of a preferred embodiment of the present tissue ablation device assembly. The illustrated embodiment is intended to illustrate, and not to limit the invention. The drawings contain the following figures.

FIG. 2A is an enlarged cross-sectional view of a section of the ablation member of FIG. 2 taken along line 2A—2A.

FIGS. 4A–4D illustrate other variation of electrode configurations that can be used with the ablation member of FIG. 3.

FIG. 5 is a cross-sectional, side elevational view of an irrigated ablation member configured in accordance with another preferred variation of the present invention.

FIG. 6 is a cross-sectional, side elevational view of an irrigated ablation member configured in accordance with an additional preferred variation of the present invention.

FIG. 6A is a cross-sectional view of the ablation member of FIG. 6 taken along line 6A—6A.

FIG. 8 is a cross-sectional, side elevational view of an irrigated ablation member configured in accordance with another preferred variation of the present invention, with a fluid effluent port located on a distal end of the irrigated ablation member.

FIG. 9 is a cross-sectional, side elevational view of an irrigated ablation member configured in accordance with an additional preferred variation of the present invention, with a slideable fluid delivery tube positioned within the ablation member.

FIG. 10 is a cross-sectional, side elevational view of an irrigated ablation member configured in accordance with another preferred variation of the present invention, similar to that shown in FIG. 9, with the addition baffles arranged on proximal and distal sides of effluent openings in the fluid delivery tube.

FIG. 14 is a schematic illustration of another variation of an irrigated tissue ablation device assembly in accordance with another preferred variation of the present invention.

FIG. 15 is a schematic illustration of the device illustrated in FIG. 14 with an exemplary catheter positioned within the device

DETAILED DESCRIPTION OF PREFERRED EMBODIMENTS

Figure 1:
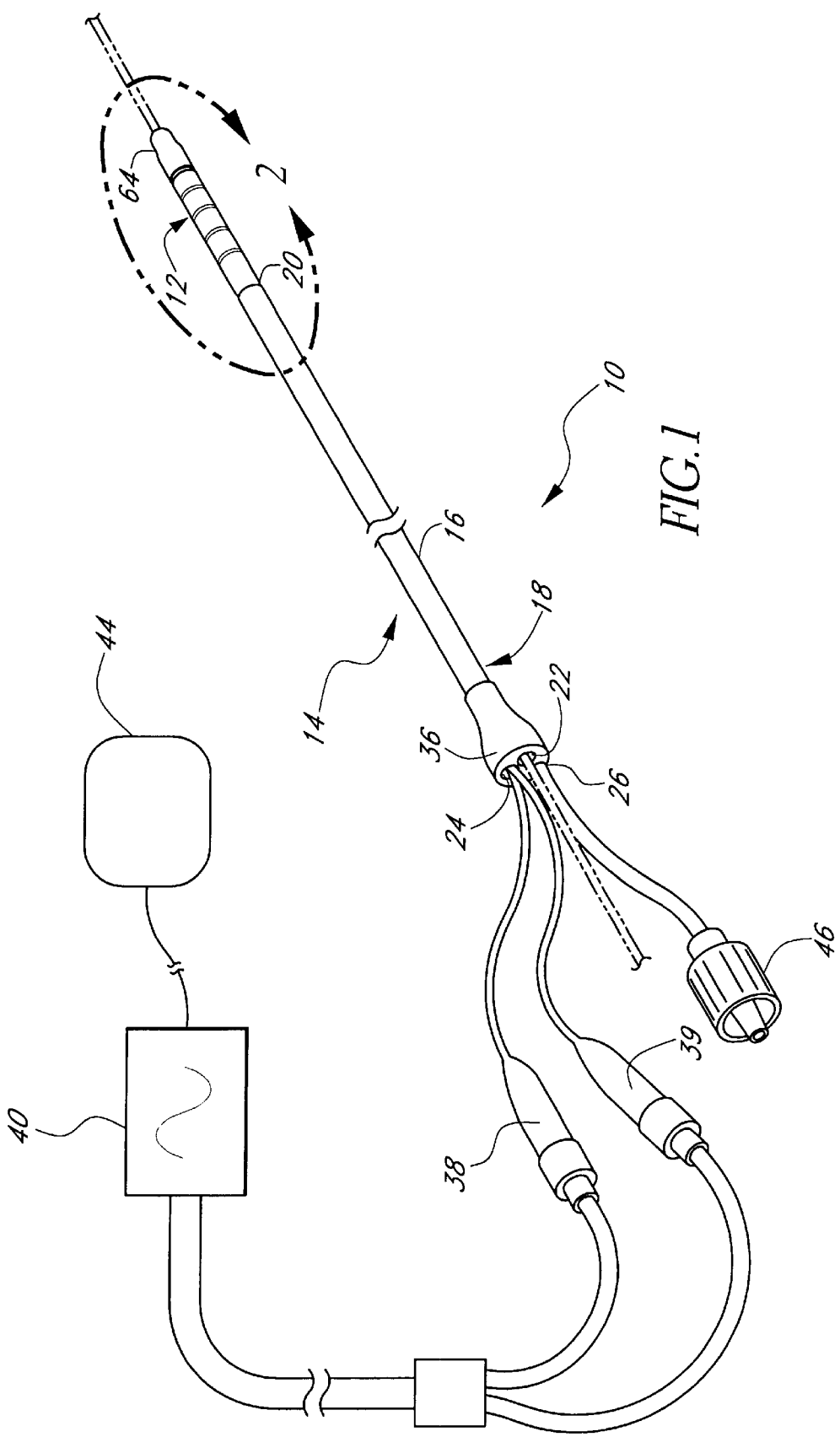
FIG. 1 is a perspective view of a tissue ablation device assembly that includes an irrigated ablation member configured in accordance with a preferred variation of the present invention.

FIG. 1 illustrates a tissue ablation device assembly 10 with an irrigated ablation member 12 configured in accordance with a preferred variation of the present invention. The present ablation member 12 has particular utility in connection with forming a linear lesion within myocardial tissue of a left atrium of a mammal's heart. The application of the present ablation member, however, is merely exemplary, and it is understood that those skilled in the art can readily adapt the present irrigated ablation member 12 for applications in other body spaces, as well as to ablate other shape lesions.

The ablation member 12 is attached to a delivery member 14 in order to access and position the ablation member 12 at the site of the target tissue. In the illustrated mode, the delivery member takes the form of an exemplary over-the-wire catheter. The delivery member 14 comprises an elongated body 16 with proximal 18 and distal end portions 20. As used herein, the terms "distal" and "proximal" are used in reference to a source of fluid located outside the body of the patient. The elongated body 16 includes a guidewire lumen 22, an electrical lead lumen 24 and a fluid lumen 26, as described in greater detail below.

Each lumen extends between a proximal port and a respective distal end 20. In the illustrated mode, the distal ends of the lumens extend through the ablation member 12, as described in greater detail below. Although the guidewire, fluid and electrical lead lumens 22, 24, 26 are illustrated in a side-by-side relationship, the elongated body 16 can be constructed with one or more of these lumens arranged in a coaxial relationship, or in any of a wide variety of configurations that will be readily apparent to tone of ordinary skill in the art.

The elongated body 16 of the delivery member and the distally positioned ablation member 12 desirably are adapted to be introduced into the left atrium, preferably by a percutaneous translumenal procedure, and more preferably in a transeptal procedure. Therefore, the distal end portion 20 of the elongated body 16 and the ablation member 12 are sufficiently flexible and adapted to track over and along a guidewire positioned within the right or left atrium, and more preferably seated within one of the pulmonary veins that communicates with the left atrium. In an exemplary construction, the proximal end portion 18 of the elongated body is constructed to be at least 30% more stiff than the distal end portion 20. According to this relationship, the proximal end portion 18 may be suitably adapted to provide push transmission to the distal end portion 20 while the distal end portion and the ablation member 12 are suitably adapted to track through bending anatomy during in vivo delivery of the ablation member 12 into the desired ablation region.

A more detailed construction for the components of the elongated body 16 which is believed to be suitable for use in transeptal left atrial ablation procedures is as follows. The elongated body 16 itself may have an outer diameter provided within the range of from about 3 French to about 11 French, and more preferably from about 7 French to about 9 French. The guidewire lumen 22 preferably is adapted to slideably receive guidewires ranging from about 0.010 inch to about 0.038 inch in diameter, and preferably is adapted for use with guidewires ranging from about 0.018 inch to about 0.035 inch in diameter. Where a 0.035 inch diameter guidewire is to be used, the guidewire lumen 22 desirably has an inner diameter of 0.040 inch to about 0.042 inch. In addition, the fluid lumen 26 desirably has an inner diameter of about 0.019 inch in order to permit ample irrigation of the ablation member 12.

Figure 2:
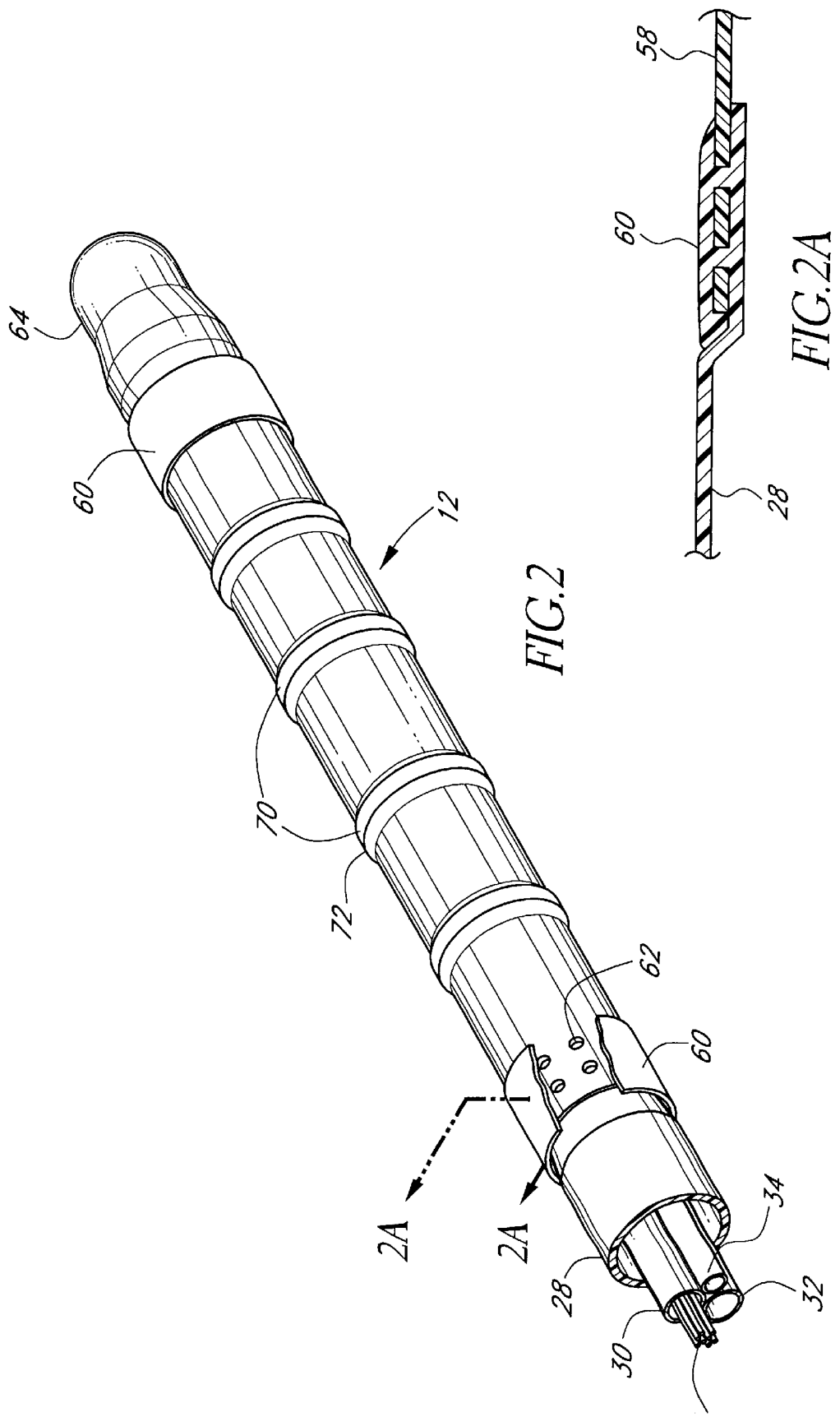
FIG. 2 is an enlarged perspective view of the irrigated ablation member of FIG. 1 with a section of the ablation member broken away.

In the illustrated mode, as best understood from FIG. 2, the elongated body 16 comprises an outer tubular member 28 that houses at least three inner tubings: an electrical lead tubing 30, a fluid tubing 32, and a guidewire tubing 34. Each of the tubings extends at least from the proximal end portion 18 of the elongated body to the distal end portion 20, and at least partially through the ablation member 12, as described below. The tubings are arranged in a side-by-side arrangement; however, as noted above, one or more of the tubings can be arranged in a coaxial arrangement. In one mode, the inner tubings are Polyimide tubes. Such tubing is available commercially from Phelps Dodge, of Trenton, Ga. The electrical lead 30 and fluid tubings 32 desirably have a 0.019 inner diameter and an 0.023 outer diameter, while the guidewire tubing 34 is slightly larger, as indicated above. The outer tubular member 28 comprises a thermoplastic, such as, for example, a urethane or vinyl material. A suitable material for this application is Pebax of a grade between 3533 to 7233, and of an outer diameter of about 0.064 inch.

Figure 3:
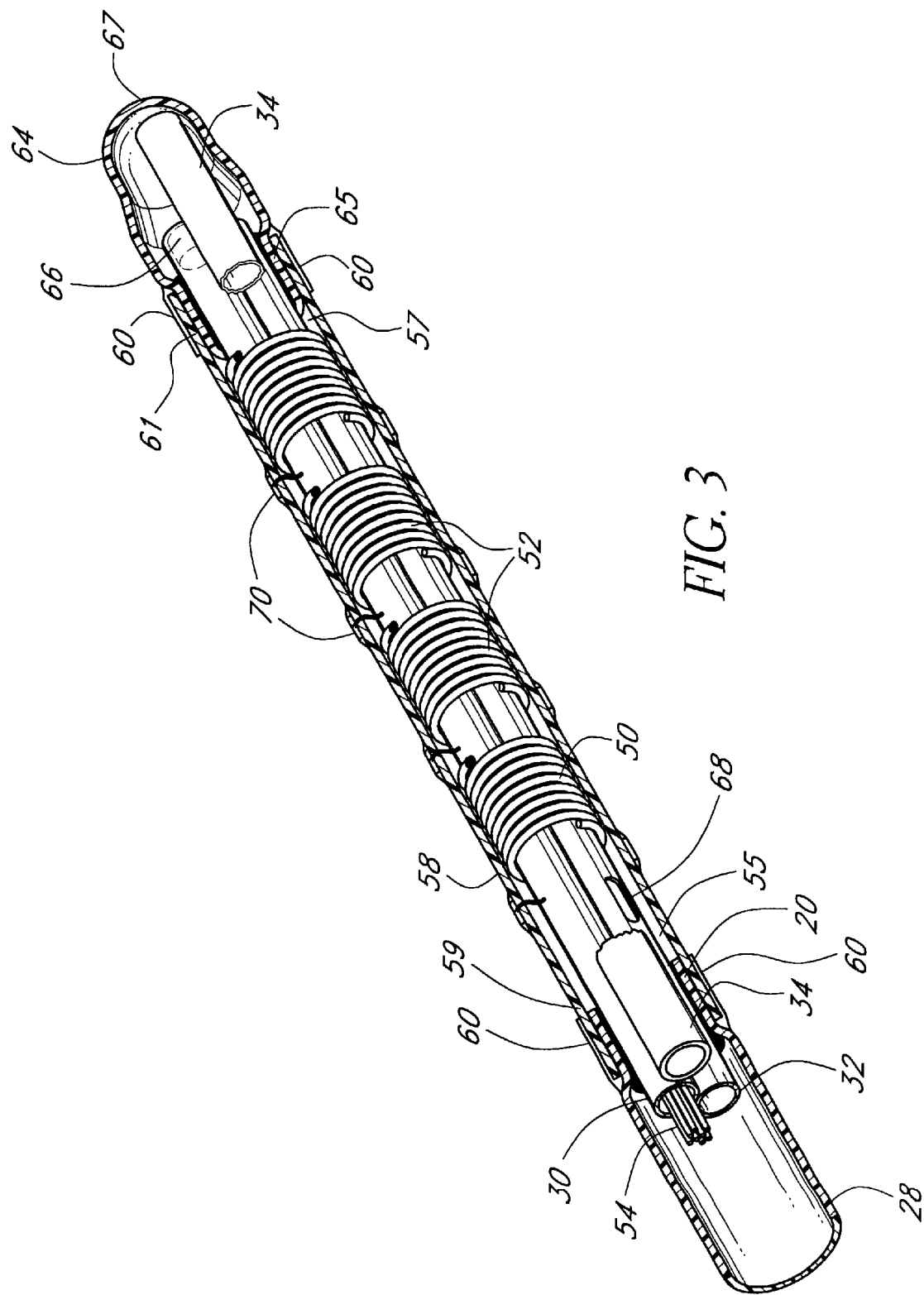
FIG. 3 is a partial cross-sectional, perspective view of the irrigated ablation member of FIG. 2, and illustrates a series of electrode coils within the ablation member.

Notwithstanding the specific delivery device constructions just described, other delivery mechanisms for delivering the ablation member 12 to a desired ablation region are also contemplated. For example, while FIGS. 1–3 illustrate a variation shown as an "over-the-wire" catheter construction, other guidewire tracking designs may also be suitable substitutes, such as for example catheter devices known as "rapid exchange" or "monorail" variations wherein the guidewire is only housed within a lumen of the catheter in the distal regions of the catheter. In another example, a deflectable tip design may also be a suitable substitute. The latter variation can also include a pullwire which is adapted to deflect the catheter tip by applying tension along varied stiffness transitions along the catheter's length.

The proximal end portion 18 of the elongated body terminates in a coupler 36. In general, any of several known designs for the coupler is suitable for use with the present tissue ablation device assembly, as would be apparent to one of ordinary skill. In the variation shown in FIG. 1, the proximal coupler 36 engages the proximal end portion 18 of the elongated body of the delivery member. The coupler 36 includes an electrical connector 38 that electrically couples one or more conductor leads, which stem from the ablation member 12 and extend through the electrical lead tube 30, with an ablation actuator 40 (schematically shown in FIG. 1). The coupler 36 also desirably includes another electrical connector 39 that electrically couples one or more temperature sensor signal wires 42 (shown in FIG. 3) to a controller of the ablation actuator 40.

As known in the art, the ablation actuator 40 is connected to both of the electrical connectors 38, 39, as schematically illustrated in FIG. 1, and to a ground patch 44. A circuit thereby is created which includes the ablation actuator 40, the ablation member 12, the patient's body (not shown), and the ground patch 44 which provides either earth ground or floating ground to the current source. In the circuit, an electrical current, such as a radiofrequency, ("RF") signal may be sent through the patient between the ablation member 12 and the ground patch 44, as well known in the art.

The coupler 36 also includes a fluid coupler 46. The fluid coupler 46 is adapted to be coupled to a source of pressurized fluid (e.g. saline solution) so as to irrigate the ablation member 12, as described below. In the variation illustrated in FIG. 1, the fluid coupler 46 communicates with the fluid tube 32 to supply the ablation member 12 with a source of pressurized fluid (not shown).

With reference now to FIGS. 1 through 3, the ablation member 12 has a generally tubular shape and includes an ablation element 50. The phrase "ablation element" as used herein means an element which is adapted to substantially ablate tissue in a body space wall upon activation by an actuator. The terms "ablate" or "ablation," including derivatives thereof, are hereafter intended to mean the substantial altering of the mechanical, electrical, chemical, or other structural nature of tissue. In the context of intracardiac ablation applications shown and described with reference to the variations of the illustrative embodiment below, "ablation" is intended to mean sufficient altering of tissue properties to substantially block conduction of electrical signals from or through the ablated cardiac tissue. The term "element" within the context of "ablation element" is herein intended to mean a discrete element, such as an electrode, or a plurality of discrete elements, such as a plurality of spaced electrodes, which are positioned so as to collectively ablate a region of tissue. Therefore, an "ablation element" according to the defined terms may include a variety of specific structures adapted to ablate a defined region of tissue. For example, one suitable ablation element for use in the present invention may be formed, according to the teachings of the embodiments below, from an "energy emitting" type which is adapted to emit energy sufficient to ablate tissue when coupled to and energized by an energy source.

Suitable "energy emitting" ablation elements for use in the present invention may therefore include, for example, but without limitation: an electrode element adapted to couple to a direct current ("DC") or alternating current ("AC") current source, such as a radiofrequency ("RF") current source; an antenna element which is energized by a microwave energy source; a heating element, such as a metallic element or other thermal conductor which is energized to emit heat such as by convection or conductive heat transfer, by resistive heating due to current flow, or an ultrasonic element such as an ultrasound crystal element which is adapted to emit ultrasonic sound waves sufficient to ablate tissue when coupled to a suitable excitation source. It also is understood that those skilled in the art can readily adapt other known ablation devices for use with the present irrigated ablation member.

In the illustrated mode, the ablation element 50 includes a plurality of electrodes 52 that are arranged over a length of the ablation member 12 next to one another (i.e., are arranged in series in the spatial sense). The length from the proximal most electrode to the distal-most electrode defines an ablation length which is less than a working length of the ablation element, as described below.

At least one conductor lead 54 connects to the electrodes 52. In the illustrated mode, the number of conductor leads 54 desirably equal to the number of electrodes 50 to allow for independent control of each electrode 50 under some modes of operation. Each conductor 54 is a 36 AWG copper wire insulated with a 0.0005 inch thick polyimide coating. Each conductor 54 exits the electrical lead tube 30 at a point near a corresponding electrode 52. A distal end of each wire is exposed and is electrically coupled to the corresponding electrode 52 in the manner described below. The proximal end of each conductor lead 54 is connected to the electrical connector 38 on the proximal end of the tissue ablation device assembly 10.

An irrigation mechanism irrigates the ablation element 50. The irrigation mechanism is adapted to provide a generally even flow of fluid about each of the electrodes along the length of the ablation member. The irrigation mechanism can be configured to discharge fluid either in a radial direction (i.e., generally normal to the longitudinal axis) or in the longitudinal direction, or in both directions, as illustrated by the below described variations of the ablation member.

The irrigation mechanism desirably includes an inner space 56 defined within a porous, fluid-permeable membrane 58. The membrane 58 desirably has a generally tubular shape and extends along at least a portion of the ablation member's length; however, the membrane 58 need not be tubular or cover the entire ablation member 12. The membrane 58 though preferably is arranged to face the target tissue once the ablation element 50 is delivered to and positioned within the particular body space. In the illustrated mode, the membrane 58 has a length, as measured in the longitudinal direction, which is greater than a distance between the proximal-most and distal-most electrodes of the series. The membrane's length is defined between its proximal 59 and distal ends 61.

The porous membrane 58 includes an inner surface and an outer surface that define the boundaries of a porous wall. The wall is formed of a porous, biocompatible, generally non-compressible material. As used herein, the term "non-compressible" means that the material generally does not exhibit appreciable or sufficient compressibility between its inner and outer surfaces to conform to surface irregularities of the tissue against which the ablation member 12 is placed. The material, however, is sufficiently flexible in the longitudinal direction (i.e., deflectable) so as to track over and along a guidewire positioned within the left atrium, and more preferably seated within one of the pulmonary veins that communicates with the left atrium. In other words, the material of the tubular porous membrane 58 allows it to bend through a winding access path during in vivo delivery of the ablation member 12 into the desired ablation region.

The porous nature of the membrane's material also permits a fluid to pass through the membrane 58 upon the application of a sufficient pressure differential across the membrane 58. Fluid thus does not freely flow through the membrane 58. The degree of porosity of the membrane 58 over its length also desirably is uniform. This uniformity coupled with the flow restrictiveness of the material results in the fluid emanating from the member 12 in a generally even flow over the entire membrane outer surface.

Exemplary porous materials suitable for this application include expanded polytetrafluoroethylene (PTFE), porous polyethylene, porous silicon, porous urethane, and tight weaves of dacron. Such porous materials are formed using conventional techniques, such as, for example by blowing the material or by drilling micro holes within the material. The porosity of the material desirably ranges between about 5 and 50 microns. An acceptable form of the porous PTFE material is available commercially from International Polymer Engineering, of Tempe, Ariz., as Product Code 014-03. It has been found that fluid will pass through this material upon applying a relatively low pressure within the material (e.g., 5 psi). In an exemplary form, the membrane 58 is formed of a tubular extrusion of this material which has an inner diameter of about 0.058 inch and an outer diameter of about 0.068 inch for applications involving ablation of myocardial tissue via an arterial or venous access path. For other applications, such as, for example, ablation within small coronary vessels, a significantly smaller diameter size can be used.

The porous membrane 58 is attached to the distal end portion 20 of the delivery member, as noted above. In illustrated mode, as best understood from FIGS. 2, 2A and 3, the proximal end 59 of the porous membrane is interposed between the distal end portion 20 of the elongated body and a sealing member 60. That is, the tubular proximal end 59 of the porous member is placed over the distal end 20 of the elongated body outer tube 28. The sealing member 60 then is slipped over this assembly and arranged to lie generally above the overlapping sections of the tube 28 and the membrane 58.

The sealing member 60 desirably is formed of a material similar to or compatible with the material of the elongated body 28 in order to heat-melt bond these two components together. In an exemplary form the sealing member 60 comprises Pebax of a similar grade used for the outer tube of the elongated body 28. This bonding process occurs with the proximal end 59 of the porous member positioned between the outer tube distal end 20 and the sealing member.

The porous membrane 58 also desirably includes one or more openings 62 that extend through the wall of the porous membrane. These openings 62 are formed (e.g., punched) on the proximal end of the membrane 58 prior to the bonding procedure, and can take the form of holes or longitudinal slots that extend into the membrane from the proximal end; of course, other shapes of openings can also be used. As best illustrated in FIG. 2A, the similar plastic materials of the seal member 60 and the elongated body outer tube 28 fuse together within these openings and bond under and over the porous material of the membrane 58 during the bonding process. This coupling securely attaches the porous membrane 58 to the distal end portion 20 of the elongated body 28.

The porous membrane 58 of course can be joined to the distal end portion 20 of the elongated body in any of a variety of other ways well known to those skilled in the art. For instance, the proximal end 59 of the porous membrane 58 can be bonded to the outer tube distal end 20 using a biocompatible adhesive, such as, for example, cyanoacrylate available commercially from Loctite® of Rockyhill, Conn., as Part No. 498.

An end cap 64 closes the distal end of the porous membrane 58. The end cap 64 desirably has a tapering shape which decreases in diameter distally. On its distal end, the end cap 64 includes a port which aligns with the distal end of the guidewire tube 34 when assembled. The end cap 64 also includes an inner opening defined in part by a collar section 65. The inner diameter of the collar section 65 is sized to receive the distal ends of the tubings 30, 32, 34, and the outer diameter of the collar is sized to slip within the distal end 61 of the porous membrane.

The end cap 64 desirably is formed of a biocompatible plastic material, such as, for example, urethane or vinyl. In a preferred mode, the end cap 64 is formed of same material that comprises the outer tube of the elongated body, such as, Pebax of a grade between 3533 to 7233, and of an outer diameter of about 0.064 inch.

The end cap 64 and the distal end 61 of the porous membrane 58 desirably are secured together in a similar fashion to that described above. As such, a heat melt bond is formed between a second sealing member 60 and the distal end cap 64, with the distal end of the porous member 58 being interposed between these elements. The similar plastic materials of the sealing member 60 and the end cap 64 fuse together within openings in the porous membrane at its distal end, as well as over and under the porous membrane. Other bondings can also be used as described above.

As best understood from FIG. 3, the guidewire tube 34, the fluid tube 32, and the lead wire tube 30 each extend within the porous membrane 58 in a longitudinal direction to the distal end cap 64.

The electrical lead tube 30 functions as a wiring harness and carries one or more conductors 54 or wires that are attached to the electrodes 52. In the illustrated mode, the tube extends beyond the distal end portion of the elongated body, through the porous membrane 58 and terminates at a point within the distal end cap 64. A plug 66 seals the distal end of the electrical lead tube. In an exemplary form, the plug 66 is formed by filling the distal end of the tube with Cyanoaerylat®.

The guidewire tube 34 extends entirely through the ablation member 12 and the distal end cap 64, and communicates with a distal port 67 formed in the end cap. The distal port 67 is sized to receive the guidewire over which the elongated body 16 and the ablation member 12 track. The port, thus, allows the guidewire to pass through the end cap 64. In a variation of the design depicted, the guidewire tube 34 can replace the end cap with the porous membrane attaching directly to the tube 34. In such an embodiment, the other tube will stop short of the distal end of the ablation member.

The fluid tube 32 defines a pressurizable fluid passageway. In the illustrated mode, the fluid tube 32 extends beyond the distal end portion of the elongated body, through the porous membrane 58 and terminates at a point within the distal end cap 64 next to a distal end of the electrical lead tube. Another plug seals the distal end of the fluid tube. In an exemplary form, the plug is formed by filling the distal end of the tube with Loctite®. The tube 32, however, can terminate proximal of the electrodes 50 but distal of the proximal membrane seal.

The fluid tube 32 includes at least one opening 68 which opens into the inner space 56 defined within the porous membrane 58. In this manner, the pressurizable fluid passageway or lumen provided by the irrigation tube communicates with the inner space 56 of the ablation member. In the illustrated mode, a single slot 68 is formed near a proximal end of the inner space 56; however, several slots or holes can be formed along the section of the irrigation tube that extends through the inner space. In a variation of the illustrated mode, the elongated body 16 also includes a return passageway that communicates with at least a portion of the inner space 56 within the porous membrane 58.

A proximal end 55 of the inner space desirably is sealed to prevent a flow of fluid proximally. In the present variation, the distal end 57 of the inner space is also sealed. This allows the pressure within the inner space 56 to be increased to promote fluid weeping through the wall of the porous membrane 58, as described in greater detail below. The above described sealing technique provides an adequate seal. In the alternative, a seal can be formed at each location by heat shrinking polyethylene teraphthalate (PET) over the tubes. The proximal seal has an outer diameter of a sufficient size to plug the passage through the elongated body at the distal end of the body and the distal seal has an outer diameter of sufficient size to plug the opening defined by the collar in the distal end cap 64.

As seen in FIG. 3, each electrode 52 in the illustrated construction comprises a wire coil formed in a helical pattern. The electrodes 52 desirably have identical configurations, and thus, the following description of one is understood to apply equally to all, unless indicated otherwise.

Each coil electrode 52 has a sufficiently large inner diameter to receive tubings 30, 32, 34, while its outer diameter is sized to fit within the tubular porous membrane 58. In an exemplary form, each ablation element 50 comprises a 0.005 inch diameter wire made of a biocompatible material (e.g., stainless steel, platinum, gold-plated niteinol, etc.). The wire is unshielded and is wound in a helical fashion with about a 0.048 inch inner diameter. The coils 52 are spaced along the lengths of the tubings 30, 32, 34 that extend longitudinally through the porous membrane 58. In an exemplary mode, each coil 52 has a length, as measured in the longitudinal direction, of about 0.28 inch and is spaced from an adjacent coil by a distance of about 0.08 inch.

The corresponding conductor wire 54 passes through a hole in the electrical lead tubing 30 and is soldered to the coil with a 95 Ag/5 Sn. The conductor wire 54 can also be electrically connected to the electrodes 50 by other means, such as, for example, by resistant, ultrasonic or laser welding. In addition, the coil and the conductor can be unitary by winding the distal end of the conductor in a helical pattern. Known electrical connectors can also be used to electrically couple the conductor to the corresponding electrode.

Figure 4A:
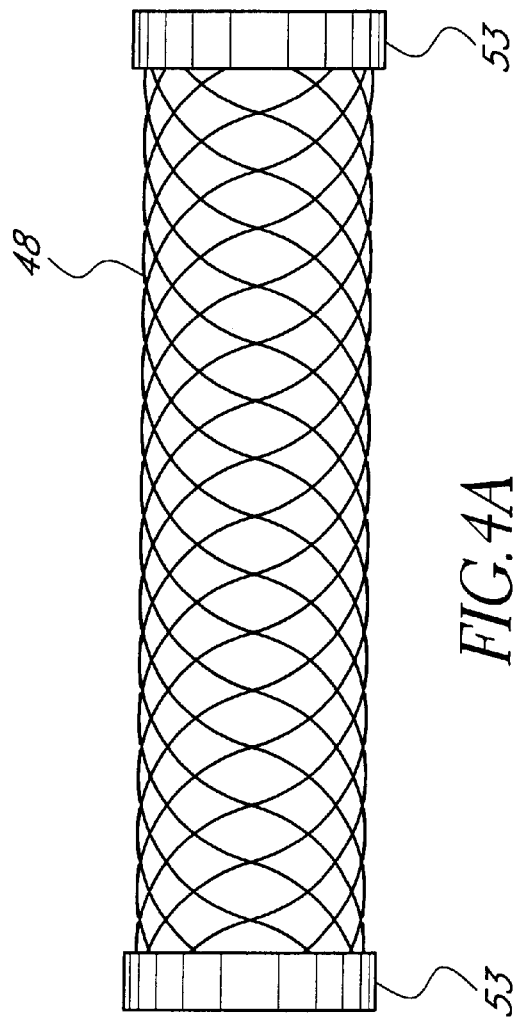

The electrodes 52 of the ablation member desirably have sufficient flexibility to bend to track through a venous or arterial access path to an ablation target site. The coil construction illustrated in FIG. 3 provides such flexibility. The electrodes 53 can, however, have other configurations which also afford similar flexibility. For instance, as seen in FIG. 4A, the electrode 48 can have a tubular or cylindrical shape formed by a plurality of braided wires. The end bands 53 link the ends of the wires together to prevent the braided structure from unraveling. The end bands 53 can also electrically couple the wires together. The bands though are sufficiently narrow so as not to meaningfully degrade the flexibility of the ablation element 50. Any braided pattern can work, but a "diamond" pattern mesh is preferred. The wires of the braid can either have rectangular ("flat") or rounded cross sections. The wire material can be any of a wide variety of known biocompatible materials (such as those identified above in connection with the coil electrodes). In one mode, the braided electrode can be "wounded" before inserting into the tubular porous membrane. Once inserted, the electrode can be uncoiled to press against the inner surface of the tube. In this manner, the membrane can support the electrode.

Figure 4B:
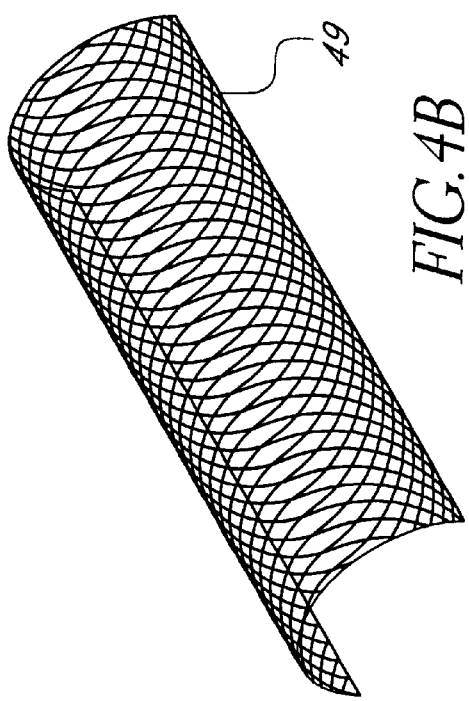

FIG. 4B illustrates an electrode construction where the electrode 49 is formed from a flat wire mesh which has been rolled into an arcuate structure. In the illustrated form, the structure has a semi-cylindrical shape; however, the structure can extend through either more or less of an arc.

FIG. 4C illustrates an electrode 51 of a "fishbone" pattern. The electrode 51 includes a plurality of arcuate segments that extend from an elongated section which generally lie parallel to a longitudinal axis of the ablation member when assembled. The ends of each arcuate segment can be squared (as illustrated) or rounded.

FIG. 4D illustrates an electrode 72 formed in an "arches" pattern. A plurality of arch segments lie in series with two side rails 74 interconnecting the corresponding ends of the arch segments. The arch segments are spaced apart from one another along the length of the electrode. The electrode embodiments illustrated in FIGS. 4C and 4D can be formed by etching or laser cutting a tube of electrode material.

Common to all of the illustrated electrodes is the ability to flex. The flexibility of these electrodes allows them to bend through tight turns in the venous or arterial access path without collapsing. The electrodes also have low profiles so as to minimize the outer diameter of the ablation member 12. Fluid also can pass radial through the electrodes 52. Other types of electrode designs which exhibit these features can also be used. For example, the electrode 52 can be formed in a manner resembling a conventional stent by etching or laser cutting a tube. The electrode also need not extend entirely about the longitudinal axis of the ablation member;

the electrode can be generally flat and positioned on only one side of the catheter. A serpentine shape would provide such a flat electrode with the desired flexibility. However, in order for the ablation member to be less orientation sensitive, each electrode desirably extends through at least 180 degrees about the longitudinal axis of the ablation member. Accordingly, the foregoing electrode designs are merely exemplary of the types of electrodes that can be used with the present ablation member.

Although the following variations of the irrigation ablation member 12 are described as including a coiled electrode 52, it is understood that any of foregoing designs, as well as variations thereof, can be used as well with these devices.

The tissue ablation device assembly 10 also desirably includes feedback control. For instance, the ablation member 12 can include one or more thermal sensors 70 (e.g., thermocouples, thermisturs, etc.) that are provided to either the outer side or the inside of the porous membrane 58. Monitoring temperature at this location provides indicia for the progression of the lesion. The number of thermocouples 70 desirably equals the number of electrodes 52 so as to enhance the independent control of each electrode. If the temperature sensors are located inside the porous membrane 58, the feedback control may also need to account for any temperature gradient that occurs across the membrane.

The sensors placed on the exterior of the porous member may also be used to record electrogram signals by reconnecting the signal leads to different input port of the signal processing unit. Such signals can be useful in mapping the target tissue both before and after ablation.

In the illustrated embodiment, the temperature sensors 70 each comprise an annular thermocouple that is positioned about the outer side of the porous membrane 58. In this location, the thermocouple 70 lies on the outside of the membrane 58 where it can directly contact the tissue-electrode interface. The thermocouple 70 is isolated from direct metal-to-metal electrical contact with the electrodes 52 because the thermocouples are separated by the porous membrane 58. Thus, separate insulation is not necessary.

As understood from FIG. 2, the thermocouples 70 desirably are blended into the outer surface of the ablation member 12 in order to present a smooth profile. In the illustrated mode, transition regions 72, which are formed by either adhesive or melted polymer tubing, "smooth out" the surface of the ablation member 12 as the surface steps up from the porous member outer surface to the thermocouple surface.

Signal wires 42 extend proximally from the thermocouples 70 to the electrical connector 39 on the proximal end of the tissue ablation device assembly 10. In the illustrated mode, the wires 42 are shielded and extend into the porous membrane 58 and then into the electrical lead tube 36. These wires 74 can be routed proximally in other manners. For instance, the wires 74 can form a braided structure on the exterior of the ablation member 12 and then be pulled together and routed proximally along the side of the elongated body. The wires 74 can also be routed proximally inside one or more tubes that extend parallel to and are attached to the elongated body. The wires 74 can also be sewn into the wall of the outer tubing of the elongated body. These represent a few variations on various ways of routing the thermocouple wires to the proximal end of the tissue ablation device assembly.

In use, the electrical and fluid connectors of the proximal coupler are connected to the ablation actuator and the pressurized fluid source, respectively. A conventional grounding patch or other grounding device is placed against the patient.

A patient diagnosed with focal arrhythmia originating from an arrhythmogenic origin or focus in a pulmonary vein may be treated with a tissue ablation device assembly 10 of the present invention by using the assembly 10 to form a longitudinal conduction block along a path of the wall tissue of the pulmonary vein that either includes the arrhythmogenic origin or is between the origin and the left atrium. In the former case, the arrhythmogenic tissue at the origin is destroyed by the conduction block as it is formed through that focus. In the latter case, the arrhythmogenic focus may still conduct abnormally, although such aberrant conduction is prevented from entering and affecting the atrial wall tissue due to the intervening longitudinal conduction block.

The ablation method of the present invention includes positioning an ablation element 50 at an ablation region along the pulmonary vein and ablating a continuous region of tissue in the pulmonary vein wall at the ablation region.

In positioning the ablation element 50 at the ablation region, a distal tip of a guiding catheter is first positioned within the left atrium according to a transeptal access method, which will be described in more detail below, and through the fossa ovalis. The right venous system is first accessed using the "Seldinger" technique, wherein a peripheral vein (such as a femoral vein), is punctured with a needle and the puncture wound is dilated with a dilator to a size sufficient to accommodate an introducer sheath. An introducer sheath, which has at least one hemostatic valve, is seated within the dilated puncture wound while relative hemostasis is maintained. With the introducer sheath in place, the guiding catheter or sheath is introduced through the hemostatic valve of the introducer sheath and is advanced along the peripheral vein, into the region of the vena cavae, and into the right atrium.

Once in the right atrium, the distal tip of the guiding catheter is positioned against the fossa ovalis in the intraatrial septal wall. A "Brochenbrough" needle or trocar is then advanced distally through the guiding catheter until it punctures the fossa ovalis. A separate dilator can also be advanced with the needle through the fossa ovalis to prepare an access port through the septum for seating the guiding catheter. Thereafter, the guiding catheter replaces the needle across the septum and is seated in the left atrium through the fossa ovalis, thereby providing access for object devices through its own inner lumen and into the left atrium.

It is also contemplated that other left atrial access methods may be utilized for using the tissue ablation device assembly of the present invention. In one alternative variation, a "retrograde" approach may be used, wherein the guiding catheter is advanced into the left atrium from the arterial system. In this variation, the Seldinger technique is employed to gain vascular access into the arterial system, rather than the venous system, such as at a femoral artery. The guiding catheter is advanced retrogradely through the aorta, around the aortic arch, into the left ventricle, and then into the left atrium through the mitral valve.

After gaining access to the left atrium, a guidewire is advanced into the pulmonary vein. This is done generally through the guiding catheter seated in the fossa ovalis. In addition to the left atrial access guiding catheter, the guidewire according to this variation may also be advanced into the pulmonary vein by directing it into the vein with a second sub-selective delivery catheter which is coaxial within the guiding catheter, such as for example, by using one of the directional catheters disclosed in U.S. Pat. No. 5,575,766 to Swartz. Alternatively, the guidewire may have sufficient stiffness and maneuverability in the left atrial cavity to unitarily subselect the desired pulmonary vein distally of the guiding catheter seated at the fossa ovalis.

Suitable guidewire designs for use in the overall tissue ablation device assembly of the present invention may be selected from previously known designs. Generally, any suitable choice should include a shaped, radiopaque distal end portion with a relatively stiff, torqueable proximal portion adapted to steer the shaped tip under X-ray visualization. Guidewires having an outer diameter ranging from 0.010 inch to 0.035 inch may be suitable. In cases where the guidewire is used to bridge the atrium from the guiding catheter at the fossa ovalis, and where in other sub-selective guiding catheters are used, guidewires having an outer diameter ranging from 0.018 to 0.035 inch may be required. It is believed that guidewires within this size range may be required to provide sufficient stiffness and maneuverability in order to allow for guidewire control and to prevent undesirable guidewire prolapsing within the relatively open atrial cavity.

Subsequent to gaining pulmonary vein access, the distal end portion of the tissue ablation device assembly 10 is tracked over the guidewire and into the pulmonary vein. The ablation element 50 is positioned at the ablation region of the pulmonary vein where the conduction block is to be desirably formed. Good contact between the ablation element and the underlying tissue facilitates the creation of a continuous transmural lesion.

Delivery of RF energy to the endocardial tissue of the pulmonary vein is commenced once the ablation member 12 is positioned at the desired ablation region. RF energy from the ablation actuator 40 is delivered to electrodes 52 via electrical leads 54. At the same time, conductive fluid, such as saline, is directed into the fluid coupler 46 and through the fluid lumen 26. In some instances, it may be desirable to begin to apply positive fluid pressure even before RF ablation is commenced in order to prevent blood accumulation in or on the ablation member 10.

In one variation, the saline passes through the openings 68 in the fluid tubing 32 to the inner space 56 within the porous membrane 58. When the pressure within the inner space 56 reaches a predetermined pressure, the fluid weeps out of the porous membrane 58. The fluid can be uniformly distributed along the longitudinal length of the ablation element 50 because the fluid does not immediately flow through the porous membrane 58, but instead remains within the inner space until the predetermined pressure is reached. This provides for both a uniform flow of fluid through the length of the porous membrane 58 and a uniform flow of RF energy along the ablation element 50. That is, the porous membrane diffuses the saline across each individual electrode, as well as across the array of electrodes. While the conductive fluid or saline is used to create a uniform conductive path between the electrodes and the target tissue, the saline can be alternatively or additionally utilized to cool the ablation electrodes 52. The fluid flows both through the helical coil of the ablation element 50 and between the plurality of ablation elements 50 of the ablation member 12, thereby facilitating the cooling of the electrodes 52 by the fluid. The bath of saline may possibly cool the electrodes so as to be capable of delivering high levels of current or be capable of longer durations to produce deeper lesions.

Once a lesion has been formed at the target spot, the guiding catheter may be repositioned and additional lesions formed.

The ablation member 12 can be constructed in other forms while obtaining the above-noted advantages. For instance, as illustrated in FIGS. 5 and 6, the ablation member 12 can include a different shaft construction from that described above. Each of these variations is described below. In the following descriptions, like reference numerals with either an "a" or a "b" suffix have been used to indicate like components between the respective ablation member and the above-described ablation member. The above description of the similar components therefore should be understood as applying equally to the components of the following embodiments, unless indicated otherwise.

With reference to FIG. 5, a guidewire tube 34a extends longitudinally through the ablation member 12a and communicates with the distal port 67a formed of the end cap 64a. The guidewire tube 34a is positioned with a structure of braided wires 76. Each of the wires is insulated, and the wires desirably are woven in a diamond-like pattern.

The braided structure 76 desirably includes at least an inner or an outer coating of a plastic material so as to define a pressurizable fluid passageway. In the illustrated form, an inner layer and an outer layer of polymer are laminated over the braid structure to define a generally fluid-impermeable structure. The polymer layers stop at the distal end 20 of the elongated body though. The braided structure 76 continues distally to form a support structure for the ablation member 12a. Fluid can pass through the uncoated braided structure.

The braided structure supports the electrodes 52a. The electrodes 52a are spaced along the length of the braided structure to define the linear ablation element. One of the wires 54a from the braid 76 is connected to a corresponding electrode 52a. Any of the above-described connectors can be used to electrically couple an unshielded end of the conductor wire to the corresponding electrode.

Although not illustrated, a spacer may be placed between adjacent electrode pairs to prevent fluid from flowing through a corresponding section of the braided structure not covered by an electrode. The spacers can be formed of a polymer or an epoxy attached directly to the braided structure. The absence of a spacer, however, provides a fluid flow between the electrodes 50 that may be beneficial in some applications.

The porous membrane 58a covers the electrodes 52a supported by the braided structure 76. A proximal end 59a of the porous membrane is secured to the distal end 20a of the elongated body, as defined by the distal end of the laminate structure. The proximal end 59a of the porous membrane can be attached in any of the above described manners.

Similarly, the distal end 61a of the porous membrane 58a is attached to the end cap 64a. The end cap 64a includes an elongated collar 65a that receives a distal end of the braided structure. The distal end of the porous membrane 61a extends over the collar 65a and is secured thereto in any of the above described manners.

The ablation member 12a can also include one or more thermocouples. The thermocouples 70a are attached to the porous membrane 58a in the manner described above. In the illustrated variation, the thermocouple wires 42a extend through the membrane 58a and through the braided structure 76, and are routed proximally through the inner lumen of the braided structure that defines the pressurizable fluid passageway. The proximal end of the thermal couple wires are connected to an electrical connector of a proximal coupler (such as that illustrated in FIG. 1).

The variation of the ablation member 12b illustrated in FIG. 6 involves an extruded shaft 82 including a plurality of lumens. The shaft can be formed of Pebax or another suitably flexible thermoplastic. As best seen in FIG. 6A, the shaft 82 includes three lumens: a guidewire lumen 22b, a fluid lumen 26b, and an electrical lead lumen 24b. Although the lumens are arranged in a side-by-side arrangement, two or more of the lumens 22b, 24b, 26b can have a coaxial arrangement. Plugs 66b close the distal ends of the electrical lead lumen 24b and the fluid lumen 26b.

The shaft 82 supports the electrodes 52b. The electrodes 52b are spaced along the length of the shaft 82 to define the linear ablation element 50b. A conductor lead 54b extends through the wall of the shaft 82 from the electrical lead lumen 24b at a point near the corresponding electrode 54b. Any of the above-described connectors can be used to electrically couple an unshielded end of the conductor wire to the corresponding electrode 52b. Each of the electrical leads 54b is connected to the proximal coupler 36 located at the proximal end of the tissue ablation device assembly (see FIG. 1).

The porous membrane 58b covers the electrodes 52b supported by extrusion shaft 82. A proximal end 59b of the porous membrane is securely sealed about the outer surface of the shaft 82, and the distal end 61b of the porous member is securely sealed about the shaft at a point proximal of the distal end of the shaft 82. The ends of the porous membrane can be attached to the shaft in any of the above described manners.

The ablation member can also include one or more thermocouples 70b. The thermocouples 70b are attached to the porous membrane 58b in the manner described above. In the illustrated variation, the thermocouple wires 42b extend through the membrane 58b and through a hole in the shaft 82 that opens into the electrical lead lumen 30b, and are routed proximally through the lumen 30b. The proximal end of the thermal couple wires 42b are connected to an electrical connector 38 of a proximal coupler 76 (such as that illustrated in FIG. 1).

The shaft 82 also includes an opening 68b located just distal of the annular attachment of the proximal end 59b of the porous member to the shaft 82. The opening 68b extends from the fluid lumen 26b and opens into an inner space 56b defined within the porous membrane 58b. In this manner, fluid can flow from the fluid lumen 24b and into the inner space 56b so as to pressurize the inner space 56b before passing through the membrane 58b in the manner described above.

Figure 7:
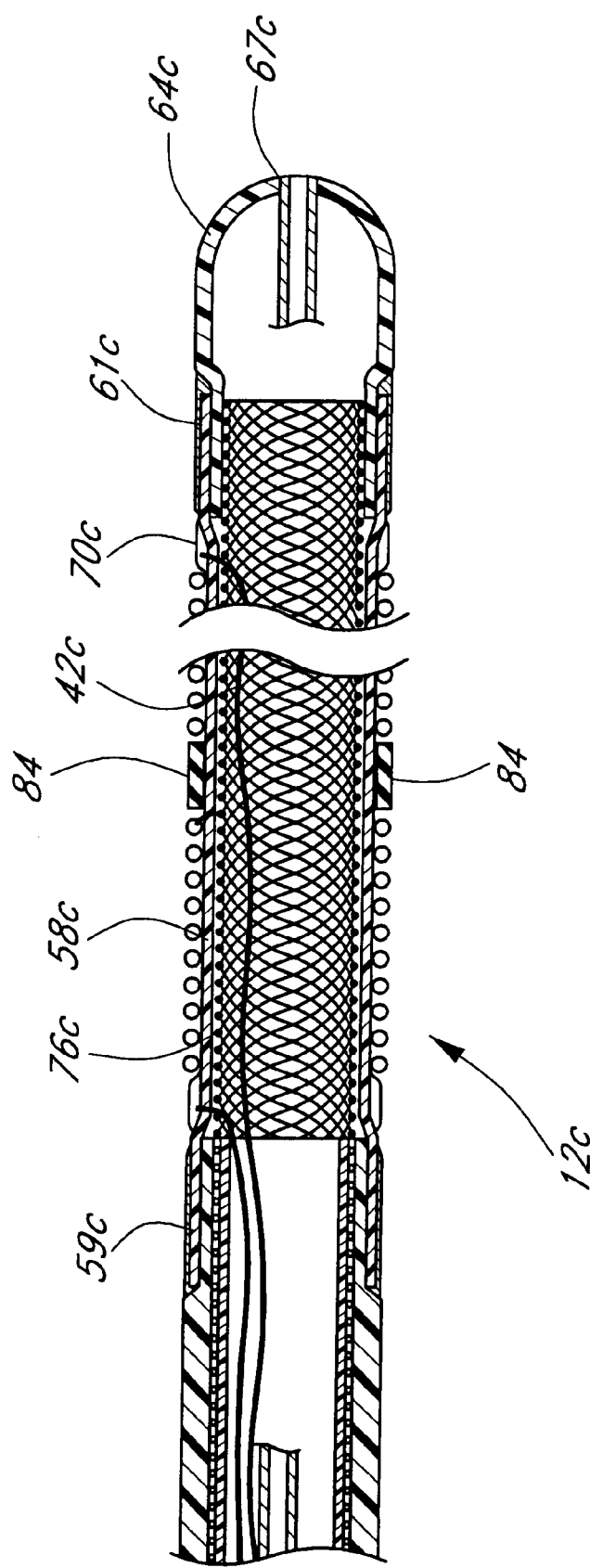
FIG. 7 is a cross-sectional, side elevational view of an irrigated ablation member configured in accordance with another preferred variation of the present invention, with the electrode elements positioned on an outer side of a porous membrane.

In each of the above described variations of the ablation member 12, the porous membrane 58 covers the electrodes 52. The porous membrane, however, can lie inside or beneath the electrodes while still providing an even flow past each of the electrodes. This modification can be incorporated into each of the variations described above. Thus, by way of example, FIG. 7 illustrates the porous membrane 58c located between the electrodes 52c and the braided structure 76c. In other respects, however, the general construction of the ablation member 12c is generally the same as the ablation member shown in FIG. 5. Accordingly, like reference numbers with a "c" suffix have been used in indicate like components between these two embodiments. The foregoing description of such like components also is meant to apply unless indicated otherwise.

As seen in FIG. 7, the porous membrane 58c lies atop the braided structure 76c. The electrodes 52c are placed about the braided structure 76c and the porous membrane 58c. As illustrated in FIG. 7, the ablation member 12c desirably includes a reduced diameter section in which the electrodes 52c reside to maintain a generally uniform profile along the distal end of the tissue ablation device assembly. Spacers 84 can also be positioned within this section to lie between adjacent pairs of electrodes. As noted above, such spacers 84 prevent fluid from flowing through the porous membrane 58c at locations other than those about which an electrode 52c is located. The ablation member, however, can be configured without spacers so as to provide a fluid flow between adjacent electrodes 50a.

FIGS. 8–10 illustrate further variations of the ablation member. With reference now to FIG. 8, the illustrated ablation member has a construction similar to that of illustrated in FIG. 7. Again, like reference numerals with a "d" suffix have been used in to indicate similar components between these embodiments, with the understanding that the foregoing description should apply equally to the such component of the present variation, unless noted otherwise.

In the illustrated variation, the distal end 85 of the ablation member 12d is open; however, it desirably has a tapering diameter 86. The smaller diameter permits some pressure to build within the fluid passageway such that at least some of the fluid within the passageway emanates radially through the braided structure 76d and the porous membrane 58d, and across the electrodes 52d. The distal end also can be rounded to ease tracking through a venous or arterial access path.

The braided structure 76d forms supports the porous membrane 58d over its entire length. Although not illustrated, other support can also be used. For example, internal or external rings can be spaced at various points along the length of the porous membrane to support further the membrane. In the alternative, a mandrel can also be used for this purpose. A proximal end of the mandrel can be embedded with the laminate structure and project in the distally.

FIG. 9 illustrates a variation on the ablation member illustrated in FIG. 8. A fluid delivery tube 90 is located within the braided structure 76d and can be moved by its proximal end (not shown) located outside the patient, so as to vary the location of the distal end of the tube 90. The distal end of the tube 90 includes one or more openings 92 which allow fluid to be delivered by the tube 90 into the pressurizable passageway. By moving the distal end of the fluid tube 90, the amount of fluid flowing across a particular electrode 52d can be varied. To further promote this effect, the fluid tube 90 can include baffles 94 located on the proximal and distal sides of the fluid openings, as seen in FIG. 10. These baffles 94 enhance a radial flow of the fluid through porous membrane 58d. Of course, these features can also be incorporated into several of the other variations described above.

The foregoing describes variations of an ablation member used to form linear ablations within a body space. The ablation member can be incorporated into a variety of delivery devices so as to locate and position the ablation member within the body space. At least one of the proximal and distal ends of the ablation member desirably is connected to the delivery device. That end is maneuverable within the body space by manipulating a proximal end of the delivery device.

Figure 11:
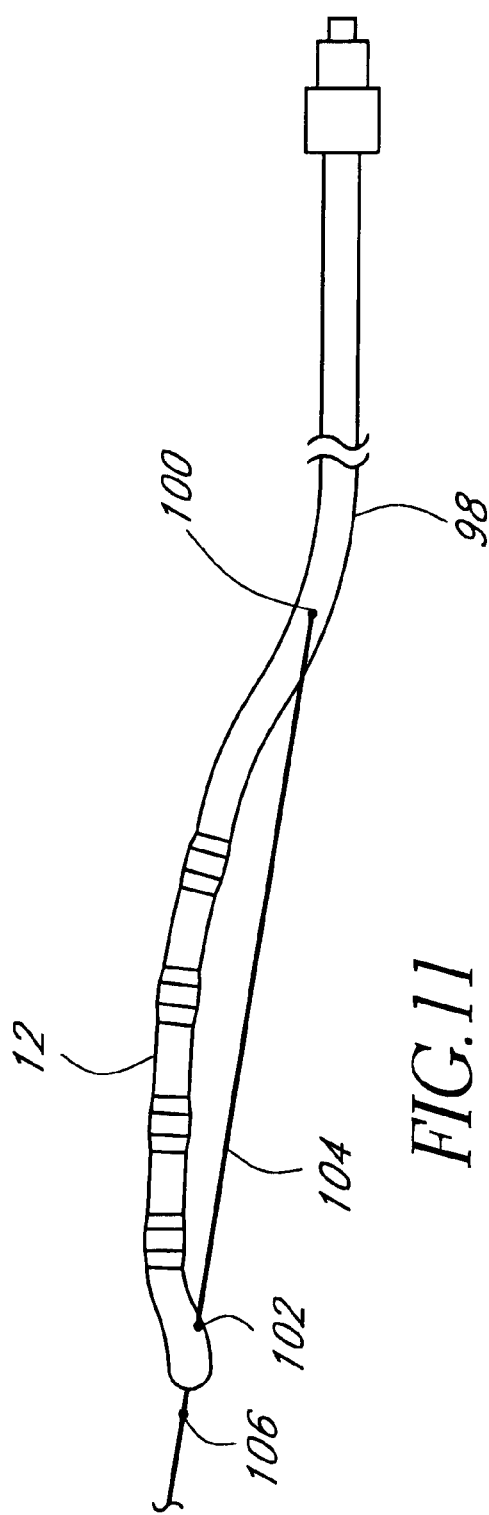
FIG. 11 is a side elevational view of an ablation member disposed on a distal end of another variation of a delivery member.
Figure 12:
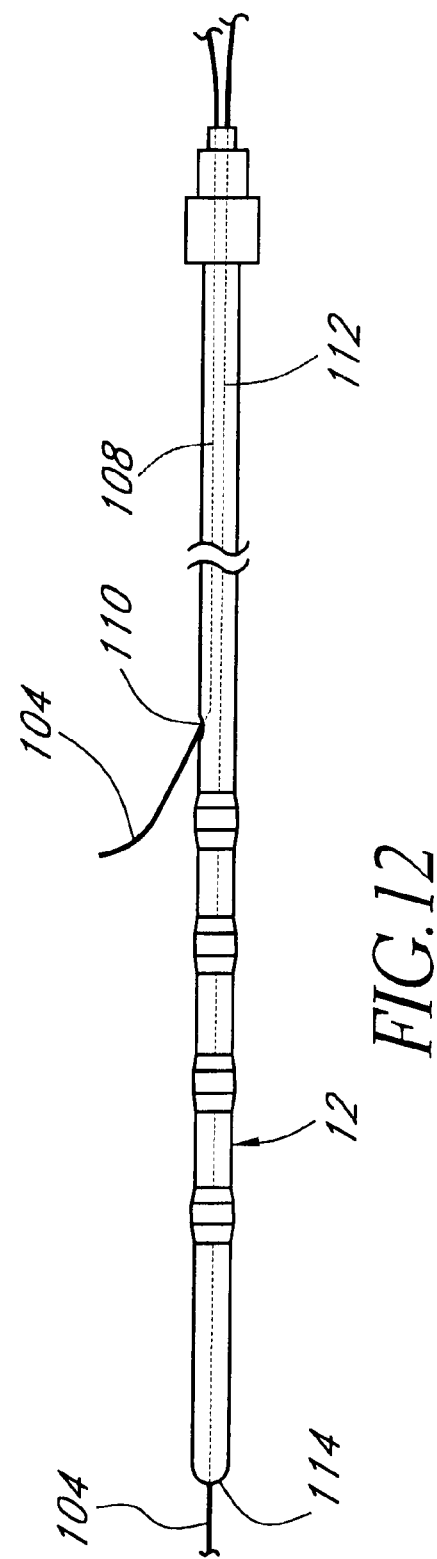
FIG. 12 is a side elevational view of an ablation member disposed on a distal end of an additional variation of a delivery member.
Figure 13:
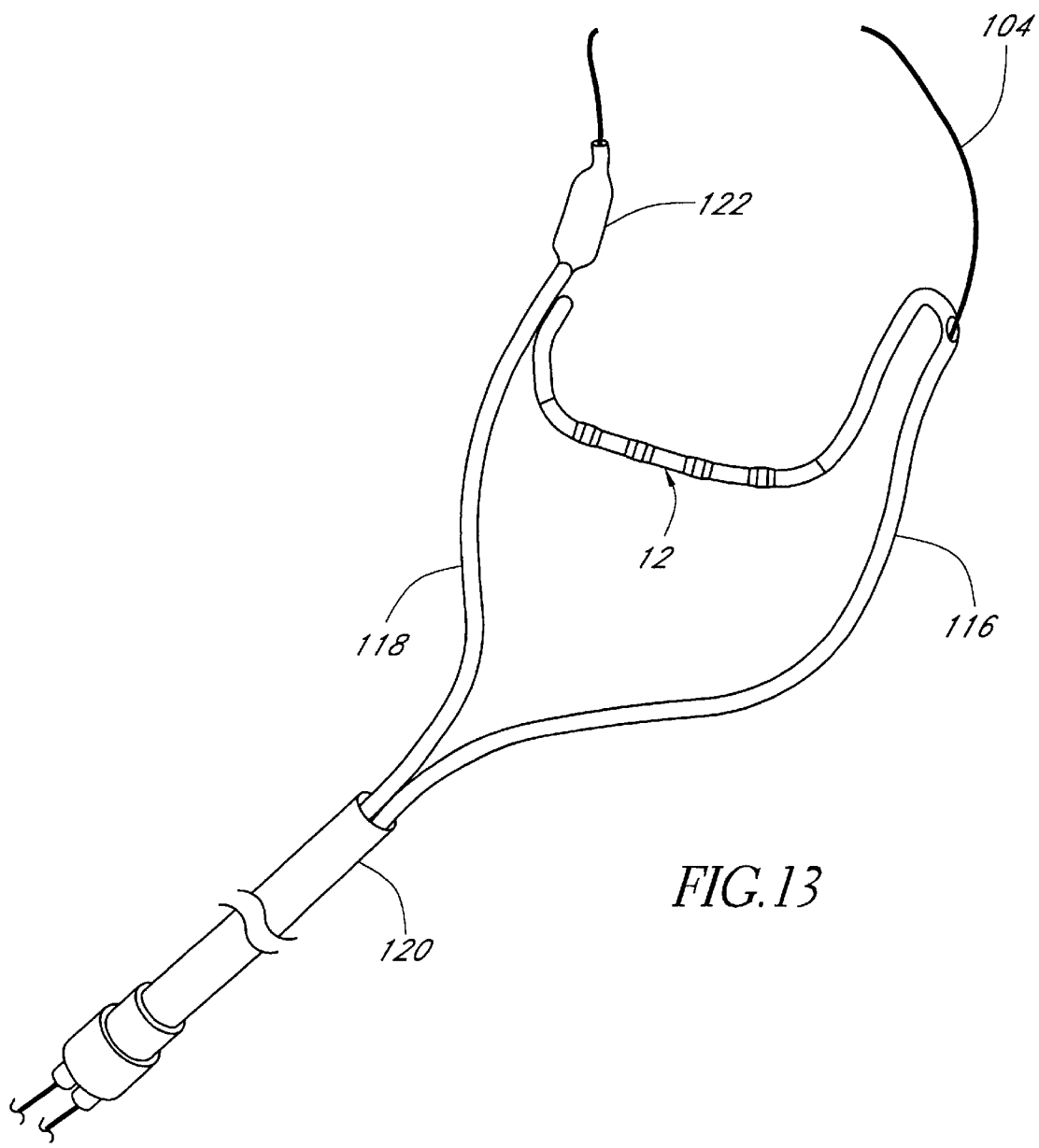
FIG. 13 is a perspective view of an ablation member arranged on a distal end portion of another variation of a delivery member.

FIGS. 11 through 13 illustrate the ablation member 12 attached to various types of exemplary delivery devices for applications within body spaces, such as, for example, the right or left atrium. In FIG. 11, the ablation member 12 is attached to a distal end of an elongated catheter body 98. The body 98 includes a guidewire port 100 proximal of the ablation member 12. The distal end of the device also includes a lumen section 102 or guidewire tracking member that also receives and tracks over the guidewire 104. A stop 106 is formed on the guidewire 104. At a desired location, the distal end of the ablation member 12 can contact the stop 106. Further distal movement of the elongated body 98 and the ablation member 12 causes the ablation member 12 to bow outward away from the guidewire 104.

FIG. 12 illustrates another variation of a delivery member. The delivery member includes at least two guidewire tracking members 108, 112. A first member 108 includes an exit port 108, 110 located proximal of the ablation member 12. The first guidewire tracking member 102 also includes an inner lumen which extends proximally, either to the proximal end of the catheter for over-the-wire applications, or to a location slightly proximal of the ablation member for "rapid-exchange" applications. The second guidewire tracking member 112 includes a guidewire lumen that extends through the ablation member 12 and exits out the distal end 114 of the catheter.

FIG. 13 illustrates another variation of an exemplary delivery device. This device includes first and second delivery members 116, 118. In the illustrated mode, the delivery members 116, 118 are over-the-wire type catheters; however, other styles of catheters can also be used. The ablation member 12 is arranged between the delivery members and is attached to each delivery member near the respective distal ends. The entire assembly desirably is delivered within an outer sheath 120 that is extendible through, for example, a transeptal sheath.

In the variations of the delivery members illustrated in FIGS. 12 and 13, anchors are used to attach the ablation member to a target tissue at two locations. For instance, in the variation of the delivery devices illustrated in FIG. 12, each guidewire functions as an anchor. In applications where multiple lumens communicate with a body space, such as, for example, in the left atrium where the pulmonary veins communicate with the heart, the guidewires 104 can be routed into the lumens to function as anchors. In addition, other types of anchoring devices can also be used. For instance, an inflatable balloon 122 (such as the type illustrated in FIG. 13) or expandable baskets, can be used to secure the ablation member 12 at two locations within the targeted body space.

FIGS. 14 and 15 illustrate an additional variation of the tissue ablation device assembly. This variation permits the use of the present ablation member 12 with existing ablation and EP catheters. A flexible sheath 124 or sleeve includes at least two lumens 126, 128. One of the lumens 126 is sized to slideably receive catheter shaft of the catheter 130. The other lumen 128 is arranged next to the first lumen 126 and communicates with a fluid port 129 located on a proximal end portion of the sheath 124. The flexible body 124 can be formed by multiple tubings, a laminated braided structure or by an extruded shaft member, such as a multi-lumen type, in accordance with the various forms described above.

A porous membrane 132 is located on the distal end of the sheath. The porous membrane desirably is configured generally in accordance with one of the above variations described above in which a porous membrane 58 defines an inner space. The electrodes, however, are omitted from this embodiment. The inner space of the sheath 124 is adapted to receive a distal end of the catheter 130 which includes an ablation element 50. For this purpose, the first lumen 126 opens into the inner space. The fluid lumen also opens into the inner space to provide pressurized fluid to the space between the catheter ablation element 50 and the porous membrane 132. The distal end of the porous membrane 132 can either be closed by an end cap 134, as illustrated, or be left open, similar to the construction illustrated in FIG. 8.

In use, an electrode of the catheter 130 is positioned within the first lumen of the sheath and is advanced until the ablation element is located within the porous membrane. This preferably is done before accessing the target site; however, in some applications, the sheath can be pre-positioned or left in position with a catheter being advanced through the indwelling sheath.

In order to add the proper positioning of the ablation element 12 within the porous membrane, the catheter tip and the porous membrane desirably include indicia which correspond to each other once the distal end of the ablation member has been advanced to a point positioning it within the membrane. For in vivo applications, such indicia can take the form of radiopaque markers positioned at corresponding locations on the catheter 130 and the porous membrane 132 (or another location on the sheath).

Although this invention has been described in terms of certain preferred embodiments, other embodiments apparent to those of ordinary skill in the art are also within the scope of this invention. Accordingly, the scope of the invention is intended to be defined only by the claims that follow.

What is claimed is:

1. A tissue ablation device assembly for ablating a region of tissue in a body of a patient, comprising:

an elongated body having a proximal end portion and a distal end portion;

a tubular porous membrane located along said distal end portion, said porous membrane having a substantially non-compressible porous wall with an inner surface that defines an inner space;

an ablation element disposed within said inner space of said porous membrane, said ablation element having a fixed position with respect to said porous membrane; and a fluid passageway extending through said elongated body and communicating with said inner space, said fluid passageway being adapted to be fluidly coupled to a pressurizeable fluid source for delivering a volume of pressurized fluid from said fluid source to said inner space;

wherein said porous membrane allows at least a substantial portion of said volume of pressurized fluid to pass through said porous wall for ablatively coupling said ablation element to said region of tissue.

2. The tissue ablation device assembly of claim 1 wherein said elongated body and said tubular porous membrane are constructed for advancement through a patient's vasculature for forming a lesion in a left atrium of a heart.

3. The tissue ablation device assembly of claim 1 wherein said inner space is substantially closed in a substantially fluid tight seal such that said volume of pressurized fluid can flow from within said inner space to an external location only across said porous wall.

4. The tissue ablation device assembly of claim 3, further comprising an end cap attached to a distal end of said tubular porous membrane for sealing said distal end of said tubular porous membrane.

5. The tissue ablation device assembly of claim 1, further comprising at least one conductor coupled to said ablation element and extending proximally through said elongated body for coupling to an ablation actuator.

6. The tissue ablation device assembly of claim 5, further comprising an electrical lead lumen extending through said elongated body, said electrical lead lumen adapted for receiving said conductor.

7. The tissue ablation device assembly of claim 1, further comprising an elongated fluid tube that defines said fluid passageway, said fluid tube extending through said elongated body.

8. The tissue ablation device assembly of claim 1, further comprising at least one thermal sensor disposed along an outer surface of said porous membrane.

9. The tissue ablation device assembly of claim 8, wherein said thermal sensor is an annular temperature sensor disposed around said porous membrane.

10. The tissue ablation device assembly of claim 1 wherein said porous membrane is adapted to disperse said portion of said volume of pressurized fluid across said porous wall in a substantially uniform manner.

11. The tissue ablation device assembly of claim 1 wherein said portion of said volume of pressurized fluid is dispersed in a radial direction across said porous wall.

12. The tissue ablation device assembly of claim 1, further comprising a return passageway in communication with said inner space and extending through said elongated body, said return passageway being adapted to remove fluid from said inner space.

13. The tissue ablation device assembly of claim 1 wherein said distal end portion of said elongated body further comprises an outer surface and said porous membrane further comprises a proximal end portion which is coupled to said proximal outer surface.

14. The tissue ablation device assembly of claim 1 wherein said porous wall is made of a polytetrafluoroethylene material.

15. The tissue ablation device assembly of claim 1 wherein said ablation element comprises at least one electrode.

16. The tissue ablation device assembly of claim 15 wherein said electrode is a wire coil having a helical shape with an inner diameter adapted to receive said fluid passageway.

17. The tissue ablation device assembly of claim 15 wherein said electrode comprises at least one arcuate section that extends at least partially along a longitudinal axis of said elongated body.

18. The tissue ablation device assembly of claim 15 wherein said electrode comprises a plurality of braided wires forming a substantially tubular shape.

19. The tissue ablation device assembly of claim 1 wherein said ablation element comprises a plurality of wire coil electrodes positioned in a longitudinally spaced arrangement.

20. The tissue ablation device assembly of claim 1, further comprising a guidewire lumen extending through at least a portion of said elongated body and terminating at a distal port for slidably receiving a guidewire.

21. The tissue ablation device assembly of claim 1 wherein said elongated body further comprises an outer tubular member containing a fluid tube, an electrical lead tube and a guidewire tube, said fluid tube defining said fluid passageway, said electrical lead tube receiving a conductor coupled to said ablation element, and said guidewire tube adapted to slidably receive a guidewire.

22. The tissue ablation device assembly of claim 1 wherein said pressurizable source contains an electrolyte solution and wherein a volume of said electrolyte solution permeates across said porous wall when said volume of said electrolyte fluid is pressurized to a predetermined pressure within said inner space.

23. The tissue ablation device assembly of claim 1 wherein said proximal end portion of said elongated body is stiffer than said distal end portion for providing enhanced pushability during advancement through a patient's vasculature.

24. The tissue ablation device assembly of claim 1, further comprising first and second delivery members each having a distal end portion, said tubular porous membrane being supported between said distal end portions of said first and second delivery members, respectively.

25. The tissue ablation device assembly of claim 24, further comprising first and second anchors located at least in part along said distal end portions of said first and second delivery members, respectively.

26. The tissue ablation device assembly of claim 25, wherein at least one of said anchors comprises a guidewire tracking member which forms a bore that is adapted to slideably engage and track over a guidewire.

27. The tissue ablation device assembly of claim 25, wherein said at least one anchor comprises a guidewire having a guidewire proximal end portion, a guidewire distal end portion, and a stop on said guidewire distal end portion which has a diameter larger than said guidewire distal end portion.

28. A tissue ablation device assembly for ablating a region of tissue in a body of a patient, comprising:
　a flexible elongated body having a distal end portion and guidewire lumen for slidably receiving a guidewire;
　a tubular porous membrane having a proximal end portion bonded to an outer surface of said distal end portion of said elongated body, said porous membrane having a substantially non-compressible porous wall with an inner surface;
　an end cap attached to a distal end of said tubular porous membrane for providing a fluid tight seal in said inner space of said tubular porous membrane;
　a plurality of wire coil electrodes disposed along a longitudinal axis within said inner space of said porous membrane, said electrodes having a fixed position with respect to said porous membrane;
　a plurality of conductors coupled to said electrodes and extending through said elongated body for electrically connecting said electrodes to a current source;
　an elongated fluid tube defining a fluid passageway, said elongated fluid tube extending through said elongated body and through an inner diameter of each of said electrodes, said fluid passageway including at least one port along a distal end portion for fluid communication with said inner space, said fluid passageway being adapted for delivering a pressurized fluid from a fluid source to said inner space; and
　a plurality of thermal sensors disposed along an outer surface of said porous membrane for monitoring a temperature at said region of tissue;
　wherein said porous membrane allows at least a substantial portion of said pressurized fluid to permeate across said porous wall for ablatively coupling said electrodes to said region of tissue.

* * * * *